(12) United States Patent
Hehl et al.

(10) Patent No.: US 8,133,988 B2
(45) Date of Patent: Mar. 13, 2012

(54) TISSUE SPECIFIC PROMOTERS

(75) Inventors: Reinhard Hehl, Braunschweig (DE); Dorothee Kloos, Graefelfing (DE); Dietmar Juergen Stahl, Einbeck (DE)

(73) Assignee: KWS Saat AG, Einbeck (DE)

( * ) Notice: Subject to any disclaimer, the term of this patent is extended or adjusted under 35 U.S.C. 154(b) by 0 days.

(21) Appl. No.: 12/764,362

(22) Filed: Apr. 21, 2010

(65) Prior Publication Data
US 2010/0269226 A1 Oct. 21, 2010

Related U.S. Application Data

(62) Division of application No. 10/432,148, filed as application No. PCT/EP01/13214 on Nov. 15, 2001, now Pat. No. 7,767,801.

(30) Foreign Application Priority Data

Nov. 16, 2000 (EP) .................................. 00124989

(51) Int. Cl.
*C12N 15/63* (2006.01)
*C12N 15/00* (2006.01)
*A01H 5/00* (2006.01)
*A01H 5/10* (2006.01)

(52) U.S. Cl. ...... 536/24.1; 536/23.1; 800/287; 800/295; 435/320.1

(58) Field of Classification Search ........................ None
See application file for complete search history.

(56) References Cited

OTHER PUBLICATIONS

Feltkamp et al 1994 Plant Physiology 105:259-268.*

* cited by examiner

*Primary Examiner* — Brent T Page
(74) *Attorney, Agent, or Firm* — Patent Central LLC; Stephan A. Pendorf

(57) ABSTRACT

The invention relates to tissue specific promoters which can be used in plants for one or more of the following purposes: a. altering carbohydrate metabolism b. preventing memory substance loss c. expression of an invertase inhibitor d. expression of a fructosyl transferase e. expression of a levan sucrase f. expression of genes coding for transported proteins for N-compounds g. expression of characteristics which increase resistance/tolerance with respect to pathogens.

22 Claims, 18 Drawing Sheets

| Relative expression level | | |
|---|---|---|
| Exp.1* | Exp.2 | Average |
| 8.0 | -- | 8.0 |
| 4.5 | -- | 4.5 |
| 6.2 | 6.7 | 6.45 |
| 6.9 | 6.0 | 6.45 | pc2L-2998 —————[luciferase]

pc2L-1827 ————[luciferase]

pc2L-989 |—[luciferase]

pc2L-342 |[luciferase]

* Average of 4 treatment replicates

SEQUENCE LISTING

```
<160> NUMBER OF SEQ ID NOS: 11

<210> SEQ ID NO 1
<211> LENGTH: 4089
<212> TYPE: DNA
<213> ORGANISM: Beta vulgaris
<220> FEATURE:
<221> NAME/KEY: promoter
<222> LOCATION: (1)..(3967)
<220> FEATURE:
<221> NAME/KEY: TATA_signal
<222> LOCATION: (3860)..(3866)
<220> FEATURE:
<221> NAME/KEY: mRNA
<222> LOCATION: (3911)..(4089)

<400> SEQUENCE: 1
ctcgaggatc cttgatttgt tttttgacc  aatgagcatt aagagtgatc aagcacatgg      60
atttcaaaat atcaatggtt ggattttat  cattctcaaa tcaatggtta aagttaaata    120
ttctattttc taatttctaa atttataatt ctatactcta gtattgattt gataagcaat    180
tagtaatcta cttaaattcc taaactatta ttaataatat aaattaataa aaattataaa    240
cttagaagtt taattattat ttttaatttc aaacaagttg attgatgtaa atatgattat    300
gaatgacgtg aaacagttaa ggcaaagttg tagtttagta actttaaaaa ttagtagtgt    360
tattataact taatagaaat tataaacttt caaaattaaa ttagtattat tgattttaa     420 gaaattatta ttctaaattt ataaattcag aaatatgtga acatgttaca tgcggtgatt    480
acggattaat ttaatgctaa catgtaagac gtaacacaat aacagttaac ctactactac    540
tacttgtata ggtcttacat taatacttaa gttattggtt ataaacttat attaatatac    600
ggttatttct tctattaagc gtagatttct tataaccctta cttatacaat tatttactat    660
tactcaacta taatttgatt gtattcagtt aagtgaactt atataagtta taacaagcct    720
taatcagtac tagaccttag cttatactat actacatata cgaattttcg cttttcatat    780
tagtatctta ctgataagca ataaagttta ctacgacata gtaacaataa ttaactactt    840
gtttcaattc aattagatga tttgggtttt gaaatgaatt taacttaaag atgattacct    900
tagatagagt attgttatct tctattaagt taattactta acttacatta atacatttgt    960
tgatattatc caatatccat tatcttaaac gaacttacgc catcttgaat tagctaatcg   1020
acttacattg atacatcgat ctaatccaat attaacttgt atcaattcaa attagatgtt   1080
ttgagtttca atatgcaact taacttagag acgattaact taaatgaagc attgttatat   1140
tgaaccaatc tactgagtta tactattcta catctgtttg aattagatgc tttcggttcc   1200
gaaatgaatt caacttaaag atgattaact taagtagagt actgttatta tcttgaatta   1260
aacttagggt actgttaaac tagatgtttt gagtttcaat atgaatttaa cttagagacg   1320
attaacttaa atggagtatt gttatattga accaatctac tgagttccat tgttctacat   1380
```

-continued

```
ttgttgcaac tcaattagat gctttcagtt ccgaaatgaa ttcaacttaa aaagatgatt    1440
aacttaagta gagtactatt attatattga actagtttat cgacttacat tgatacactc    1500
attcaaataa caacatgttt caatttaagt aaacgttttg agtttcaatt actttatcga    1560
cttacgtcga tacattcatc taatctaata tcaattgtaa tttcttttag tttggctaag    1620
atatgtgagt ttcaaattga atataaattg ttagcgatta acttaaatgg agtaatgtta    1680
tcttgatttc acttatcgat tcacatagat accttgagct aatccataat caacttattt    1740
tacgtcgatt atagatatat taatccattg aactaataca ctaagagtaa gacactaaca    1800
tagatttgtc ttattccaaa tcatatatat taagtaataa agtacacttt aaccgatgtc    1860
actttcattc acgttttat gaagtacaac tattttttg aggcaattgt ggaagtgccg    1920
acaacactta tttgttgcat taattttag ccggacccga aaacacctga ccaaaaccga    1980
catgaagcac aattttccc gaacaaatac aagagtgtga ttaacttcta cccgaaccga    2040
tgcgattatt gtcgaagtta tgtggttttt tgtcaataac tgaaataaac cgaaacgaaa    2100
ctgaaaataa ccgcaacaaa ttttaactga tatggattca accgttggtt ggtttaactg    2160
tttggtaaaa actgatttaa actgcaactg aactgaactg aaaatggaaa gggaaaaaac    2220
tgaattaaac tgaactgaaa agtttgttaa ctgaactgaa ctgttaatta tttcaactaa    2280
tacaaactga actgatatca actgaactgt tggttataa ccataactga actgttgaac    2340
tgaattgaca cctctaattg caacggcaac aatagaactg ttacagtagc ccaatctaca    2400
aaactaaatt gacaagaact gttgcattag atactcctac tacaacggta cgtaataatg    2460
tgttgcacta gtaaatttta gcctttgcct ttgattaaaa atgttgtagt gacacatcac    2520
aataaaatca aatctaatga atatgctata aacaaacaat tgttccaaaa tcaactattc    2580
ttacgaaata ctcttttcga gggacgacat ttttctgaaa cacccctaagc gacgttattg    2640 actctaatac atagatgaaa tatcaataaa aagggattta tatgaggtat tctttaattt    2700 tttttaaga acatatgagg taccatagta ttttaaaaat caatccatgt gccctaact    2760 tcgtaatgta tccatcatat atatcccttt ttttttagg ggtccatcat atatatcctt    2820
aatgcatgac tatcaaacat tagatatgtc ttaatccccc cctaacaatc aaccaaaatt    2880
ccaaaattgg ttactctatt tgttcctatt acaccttcca ccaatctcaa caaattttgg    2940
cattctggtt aagtactcga aggactactt aacgaaatat ttgatgtttg ttagccatta    3000
aggtttatgt gttggattca ttataaatgg tttgaaaagt ttattatcat ctttattaaa    3060
agttcaatag tacctcatga gaactctcta taaatcaact atattagtta tcaataataa    3120
gatacattcg gattctattt ggcaacacat ttaagtcacc tcaaatgaat aggtgttaaa    3180
agtttaagtc acctaaaata aatagtcatg attaaagtaa gagcttaaat caaatgtaag    3240
ctaaaaaatt gactgaaatt aaattggtat caagtataac atcttaattt aaggtgttaa    3300
aattttcaac taacttatca attgagcttt tttcatcaat ttcacctcta tttcagcttt    3360
gtttttagct tatatttcca aaattgccaa taggtctcat ttatacctaa gatattcaac    3420
aatcctggct ctcttcctgc tcgttcattc caaatttccc aaatgtaatc agattaaagc    3480
agtagtgatc ggatcattgc agacttttcg gtagaataac tgaataagtg tactgagata    3540
gtgtcaaaat actgttattt aagttttcta taagtactaa aatatgaatt agttcaacat    3600
catcttatat tgtcggccaa taagattgcc cactgtataa taatataaaa caaaatcaca    3660
gaggtgatat cgcctaaaaa aaaaaaaatc atagatgtga attaatgtaa ccgagcataa    3720
atcaactgtt tccttttttt ttaaaagaga aatcaactgt ttcctagaaa caattgaata    3780
```

```
ttatatggtg gtttattgtt tcaaatttca gaaaaacaaa aaaaaaaaag cctttgctac        3840
ttacttacat agttgcatct atataaaggg cacctagccc aaccatttta cttacctaaa        3900
ctgtctgtgt ttgcaccact ctcatctaaa aaatctgtga agtgagcgt ttcaaaattt         3960 tcaaaagatg cacataacag gtaaattaga agttgaagtt gatatcaatt gtcatggtga        4020
tattttccat gaaattttta gcaccaggcc acatgatgtc tccaccatgt cacctgagaa        4080
tatccatgg                                                               4089

<210> SEQ ID NO 2
<211> LENGTH: 1919
<212> TYPE: DNA
<213> ORGANISM: Beta vulgaris
<220> FEATURE:
<221> NAME/KEY: promoter
<222> LOCATION: (1)..(1840)
<220> FEATURE:
<221> NAME/KEY: mRNA
<222> LOCATION: (1606)..(1919)

<400> SEQUENCE: 2
tatgatattg tcatgctgca tgcatcctca tcgtaaacaa attactccct tcgttttaaa          60
atctagttca tgtttctttt tgcacagtat taaagacata cttttgacct accacctacg         120
atatcttctt atttcatatt aataaaaaat tttaaaaagt tgatattata aatttacaca         180
ttgtggtgaa tctaacaaca cccccacatg aatatattat tttatgtaca tcagtgagag         240
tatttggtca aaaaaaataa agtttgactt ccaaaataga aacatgaact atattttgaa         300
acggccgagt gagtacttaa ttgttgttct acccatcaaa attagaaaaa aggtttttgc         360
tagtaaggaa ttctcttttt gttcgtttag gaaaagtgat aaatgataac gtctttttaa         420
tttaacgcgt gattgtgatc gtggtcctta cctgggttaa attaacatgt tcagactaca         480
ctcgtctttg ctagtggaaa ataaattgca tgttaagacg atgtttagtt ggaatgaaaa         540
acacttctct tagtatattt ggtaaaggtt gtaaaatatg gtgtgaaata aaaatctaag         600
tggagaaaca ttcaaggaaa gaatctcata atttcgttca tatccattta cttcctcttt         660
ctccatcttt tttctcttct ttctaaactt cccttcccat cactaaccaa ataatagaaa         720
gctaattaac aagtatgtat tcttttggca aaaattatta aaaaaaacag tttaatttaa         780
tataaaagta gacctagtaa ctaaataaaa aaaaaaaat aaattaaact agtcaccaaa         840
aaaaattaaa ctagtcatta ttgggctaat tttcttttta atattgcgtt taccattgtc         900 taatttaat ttaaaagtag gcggtctctt acaagataaa ctccttgagc aaatgttttt         960
ccttgagcaa atgtttttca tagaaaatct cattttctat acaatcaaac gcgcaaactc        1020
aacctaatta aagatttcgt tcagtatcac tatcaacgtt cagttttcta attggattat        1080
gattttacat atacactcat ctttatctaa aagatattaa ttgcataaac agtaaaaata        1140
taatatacaa tgataaaaaa aaattcgaag tatcactatc atctaaagag tgtattcatc        1200
atacatctgg gtgcaccatg tgcatggtac acacacgatt atttttttgct catttgaagc        1260 tctacctatt tttaattat gctcagttgg aagtttcaaa tgagcaatga gtaaaaaaaa        1320
aaccttgaat gtaccatact catgatatat ccgagtgtac cataaaaatt cccatcatct        1380
caatgtagta ctataaattt tttaataaag tccaaatatt aatagaaggg aacacatgaa        1440
aagagtagaa ttgaattagg tacataaaaa gttgcattca tatctttttc tccttggcat        1500
aacaatcttg acaatctaat ttccctattt aaatccacta acttcataga cttcatgccc        1560
caacaacagg aaagtggtct cctatccctt ttagtatcat ttcataattt caatttttaaa       1620
```

-continued

```
ttaaaagggc aattagatgg cattcttttg cattattggt attataaatt aatcatcgtg    1680
ttatctttat ctagctagaa ataccacttc caagtaaagt ttatgtcttt tgcatcatac    1740
taacaataag ccacaccatt atttcttgta cttcccttga agaaaacaaa gagaattaat    1800
agaaactaag tgagagaaag agatatagag atagtttcac atgaacatgg cttcattgcc    1860
actacaaaac ttggtcttct ttttatcatt atttctgctt cacttatatc aacttcata    1919
```

<210> SEQ ID NO 3
<211> LENGTH: 1148
<212> TYPE: DNA
<213> ORGANISM: Beta vulgaris
<220> FEATURE:
<221> NAME/KEY: promoter
<222> LOCATION: (1)..(1097)
<220> FEATURE:
<221> NAME/KEY: TATA_signal
<222> LOCATION: (950)..(956)
<220> FEATURE:
<221> NAME/KEY: mRNA
<222> LOCATION: (984)..(1148)

<400> SEQUENCE: 3

```
tctaggccta aatggccatt taggtgacac tatagaagag ctcgaggatc aacattcttc      60
tgaatcgttc ataaatacga atcttacaat atcttgtatg aatatatact atacctttt     120 atagattgaa ataaaactcc aggcgcctta tttcagattt ggagagcata atatcaacaa     180
agcaaaacat attcaaccat tatacaaacc gaaaagtttt tgatgtcact taaccaaaat     240
ttcaaaaatg atacatatgt gcagcctaag ttctatattt cacctaccta gttctataca     300
ctagcaatca taatggtcaa ttaatagtac tctcctccaa aacaacattg agtcaattag     360
agactatcgg aataggagcg aacaactaac aaatatcaac taaataatat agcggaaatc     420
tatttgtttg tcgtaataat ttttttcaat tatttttgtt tgaatattta ctcgtgtaat     480
agatgtcaat taatttagcg gtatgatttt ctaaaaagat gagctaacct aaaacttaat     540
attgtctata gcacttgcct tatggctcct aagtcctaac caccataagt tttacttggg     600
cataagatga ctcaaatcct accaatcttt catcattata actaagggct cggctatatc     660
ttcccagata tatcatggta agaaaacaca acaacctacc acctgtcaac cactagatgg     720
atagctaaga ttccacttag gaaaaatctt ccaacatggc atttaaattg gacccatatg     780
atctattaga gccaacagaa acaaaggaat agatatatgg atatggcatt agataaggat     840
agtgaaaaac acttctcatt ggctaatctt taactctcaa acccaatcta gcccttgatt     900
tccctacaac aacaaaaaaa tccaactcac taaagttcca aataactcct aaataaacaa     960
gagccacaag acttgtattg aaatgaaaat acaaggagaa gcgttacact agacaaagcc    1020
atcacaactt tgttaacact cttccttctt aatcatttcc cttcaattaa atttcttagt    1080
tgaaaccaaa atataagatg gcagcagtga caacacaggc ttcgattgcc ggattccggc    1140
catgcgca                                                             1148
```

<210> SEQ ID NO 4
<211> LENGTH: 3049
<212> TYPE: DNA
<213> ORGANISM: Beta vulgaris
<220> FEATURE:
<221> NAME/KEY: promoter
<222> LOCATION: (1)..(2998)
<220> FEATURE:
<221> NAME/KEY: TATA_signal
<222> LOCATION: (2877)..(2883)

<220> FEATURE:
<221> NAME/KEY: mRNA
<222> LOCATION: (2928)..(3049)

<400> SEQUENCE: 4

| | | | | | |
|---|---|---|---|---|---|
| ctgcagacag | cggggaatgt | caggtgctgg | cgcgatggga | cacaccgaag | gtggtgaagg | 60 |
| gcgtgagttt | cctgctccgt | ctgaccgtaa | cagcggacga | cggcagtgag | cggctggtca | 120 |
| gcacggcccg | gacgacggaa | accacatacc | gcttcacgca | actggcgctg | ggaactaca | 180 |
| ggctgacagt | ccgggcggta | aatgcgtggg | ggcagcaggg | cgatccggcg | tcggtatcgt | 240 |
| tccggattgc | cgcaccggca | gcaccgtcga | ggattgagct | gacgccgggc | tattttcaga | 300 |
| taaccgccac | gccgcatctt | gccgtttatg | acccgacggt | acagtttgag | ttctggttct | 360 |
| cggaaaagca | gattgcggat | atcagacagg | ttgaaaccag | cacgcgttat | cttggtacgg | 420 |
| cgctgtactg | gatagccgcc | agtatcaata | tcaaaccggg | ccatgattat | tacttttata | 480 |
| tccgcagtgt | gaacaccgtt | ggcaaatcgg | cattcgtgga | ggccgtcggt | cgggcgagcg | 540 |
| atgatgcgga | aggttacctg | gatttttttca | aaggcaagat | aaccgaatcc | catctcggca | 600 |
| aggagctgct | ggaaaaagtc | gagctgacgg | aggataacgc | cagcagactg | gaggagtttt | 660 |
| cgaaagagtg | gaaggatgcc | agtgataagt | ggaatgccat | gtgggctgtc | aaaattgagc | 720 |
| agaccaaaga | cggcaaacat | tatgtcgcgg | gtattggcct | cagcatggag | gacacggagg | 780 |
| aaggcaaact | gagccagttt | ctggttgccg | ccaatcgtat | cgcatttatt | gacccggcaa | 840 |
| acgggaatga | aacgccgatg | tttgtggcgc | agggcaacca | gatattcatg | aacgacgtgt | 900 |
| tcctgaagcg | cctgacggcc | cccaccatta | ccagcggcgg | caatcctccg | gccttttccc | 960 |
| tgacaccgga | cggaaagctg | accgctaaaa | atgcggatat | cagtggcagt | gtgaatgcga | 1020 |
| actccgggac | gctcagtaat | gtgacgatag | ctgaaaactg | tacgataaac | ggtacgctga | 1080 |
| gggcggaaaa | aatcgtcggg | gacattgtaa | aggcggcgag | cgcggctttt | ccgcgccagc | 1140 |
| gtgaaagcag | tgtggactgg | ccgtcaggta | cccgtactgt | caccgtgacc | gatgaccatc | 1200 |
| cttttgatcg | ccagatagtg | gtgcttccgc | tgacgtttcg | cggaagtaag | cgtactgtca | 1260 |
| gcggcaggac | aacgtattcg | atgtgttatc | tgaaagtact | gatgaacggt | gcggtgattt | 1320 |
| atgatggcgc | ggcgaacgag | gcggtacagg | tgttctcccg | tattgttgac | atgccagcgg | 1380 |
| gtcggggaaa | cgtgatcctg | acgttcacgc | ttacgtccac | acggcattcg | gcagatattc | 1440 |
| cgccgtatac | gtttgccagc | gatgtgcagg | ttatggtgat | taagaaacag | gcgctgggca | 1500 |
| tcagcgtggt | ctgagtgtgt | tacagaggtt | cgtccgggaa | cgggcgtttt | attataaaac | 1560 |
| agtgagaggt | gaacgatgcg | taatgtgtgt | attgccgttg | ctgtctttgc | cgcacttgcg | 1620 |
| gtgacagtca | ctccggcccg | tgcggaaggt | ggacatggta | cgtttacggt | gggctatttt | 1680 |
| caagtgaaac | cgggtacatt | gccgtcgttg | tcgggcgggg | ataccggtgt | gagtcatctg | 1740 |
| aaagggatta | acgtgaagta | ccgttatgag | ctgacggaca | gtgtgggggt | gatggcttcc | 1800 |
| ctgggggttcg | ccgcgtcgaa | aaagagcagc | acagtgatga | ccggggagga | tacgtttcac | 1860 |
| tatgagagcc | tgcgtggacg | ttatgtgagc | gtgatggccg | gaccggtttt | acaaatcagt | 1920 |
| aagcaggtca | gtgcgtacgc | catggccgga | gtggctcaca | gtcggtggtc | cggcagtaca | 1980 |
| atggattgcc | gtaagacgga | aatcactccc | gggtatatga | aagagacgac | cactgccagg | 2040 |
| gacgaaagtg | caatgcggca | tacctcagtg | gcgtggagtg | caggtataca | gattaatccg | 2100 |
| gcagcgtccg | tcgttgttga | tattgcttat | gaaggctccg | gcagtggcga | ctggcgtact | 2160 |
| gacggattca | tcgttggggt | cggttataaa | ttctgattag | ccaggtaaca | cagtgttatg | 2220 |

-continued

| | |
|---|---|
| acagcccgcc ggaaccggtg ggcttttttg tggggtgaat atggcagtaa agatttcagg | 2280 |
| agtcctgaaa gacggcacag gaaaaccggt acagaactgc accattcagc tgaaagccag | 2340 |
| acgtaacagc accacggtgg tggtgaacac ggtgggctca gagaatccgg atgaagcctg | 2400 |
| ctttttttata ctaagttggc attataaaaa agcattgctt atcaatttgt tgcaacgaac | 2460 |
| aggtcactat cagtcaaaat aaaatcatta tttgatttca attttgtccc actccctgcc | 2520 |
| tctgtcatca cgatactgtg atgccatggt gtccgactta tgcccgagaa gatgttgagc | 2580 |
| aaacttatcg cttatctgct tctcatagag tcttgcagac aaactgcgca actcgtgaaa | 2640 |
| ggtaggcgga tctgggtcga ctctaggcct cactggccta atacgactca ctatagggag | 2700 |
| ctcgaggatc tattagagcc aacagaaaca aggaataga tatatggata tggcattaga | 2760 |
| taaggatagt gaaaaacact tctcattggc taatctttaa ctctcaaacc caatctaacc | 2820 |
| cttgatttcc ctacaacaac aaaaaaatcc aactcactaa agttccaaat aactcctaaa | 2880 |
| taaacaagag ccacaagact tgtattgaaa tgaaaataca aggaagagcg ttacactaga | 2940 |
| caaagccatc acaactttgt taacactctt ccttcttatt tccattccaa aaaatataat | 3000 |
| ggcagcagtg acaacacagg cttcgattgc cggattccgg ccatgcgca | 3049 |

```
<210> SEQ ID NO 5
<211> LENGTH: 40
<212> TYPE: DNA
<213> ORGANISM: Artificial Sequence
<220> FEATURE:
<223> OTHER INFORMATION: Synthesized primer

<400> SEQUENCE: 5
ctgcttctaa tagagtcttg ctgcagacaa actgcgcaac                40

<210> SEQ ID NO 6
<211> LENGTH: 37
<212> TYPE: DNA
<213> ORGANISM: Artificial Sequence
<220> FEATURE:
<223> OTHER INFORMATION: Synthesized primer

<400> SEQUENCE: 6
tgaacactcg tccgagaata acgagtggat ctgggtc                  37

<210> SEQ ID NO 7
<211> LENGTH: 28
<212> TYPE: DNA
<213> ORGANISM: Artificial Sequence
<220> FEATURE:
<223> OTHER INFORMATION: Synthesized primer

<400> SEQUENCE: 7
aggttatcaa aaggcccctt tccagtca                            28

<210> SEQ ID NO 8
<211> LENGTH: 28
<212> TYPE: DNA
<213> ORGANISM: Artificial Sequence
<220> FEATURE:
<223> OTHER INFORMATION: Synthesized primer

<400> SEQUENCE: 8
gtttgtgcaa gccgagctgg tgaacgcc                            28
```

-continued

```
<210> SEQ ID NO 9
<211> LENGTH: 19
<212> TYPE: DNA
<213> ORGANISM: Artificial Sequence
<220> FEATURE:
<223> OTHER INFORMATION: Synthesized primer

<400> SEQUENCE: 9
gtggagaggc tattcggta                                                  19

<210> SEQ ID NO 10
<211> LENGTH: 20
<212> TYPE: DNA
<213> ORGANISM: Artificial Sequence
<220> FEATURE:
<223> OTHER INFORMATION: Synthesized primer

<400> SEQUENCE: 10
ccaccatgat attcggcaag                                                 20

<210> SEQ ID NO 11
<211> LENGTH: 10
<212> TYPE: DNA
<213> ORGANISM: Beta vulgaris
<220> FEATURE:
<221> NAME/KEY: misc_feature
<222> LOCATION: (4)..(7)
<220> FEATURE:
<221> NAME/KEY: misc_feature
<222> LOCATION: (4)..(7)
<223> OTHER INFORMATION: n is a, c, g, or t

<400> SEQUENCE: 11 caannnnatc                                                            10
```

TISSUE SPECIFIC PROMOTERS

BACKGROUND OF THE INVENTION

1. Field of the Invention

The present invention relates to promoters and their use in transgenetic plants.

It is possible to genetically alter crop plants by molecular biology methods, and to express proteins specifically. For this, the selection of a suitable promoter is of considerable relevance. Therefore, a great need for well-characterized promoters with specific characteristics exists.

2. Description of the Related Art

During the last years, a large number of plant promoters was isolated and analyzed for their effect. In the meantime, octopine synthase (ocs), nopaline synthase (nos) and mannopine synthase (mas) isolated from *Agrobacterium tumefaciens* and TR promoters (De Greve et al., 1982, Depicker et al., 1982; Velten et al., 1984) and 35S promoter of cauliflower mosaic virus (Odell et al., 1985) respectively, have found a broad application. Plant promoters with a constitutive activity have been described for tobacco (WO 97/28268) and raspberry (WO 97/27307).

Organ, tissue or cell specific promoters can be used for the expression of genes in specific plant parts. Specificity in this context can mean, that a promoter is mainly or exclusively active in one organ, tissue or cell type. Mainly active in a particular organ are, e.g. the tomato promoters TFM7 and TFM9 in tomato fruits (U.S. Pat. No. 5,608,150), a *brassica* promoter in roots (WO 94/02619), a sun flower promoter in seeds (WO 98/45460) and a potato promoter (WO 98/18940) in leaves. These promoters show their highest activity in the mentioned organs. An exclusive activity for a certain compartment was described for a guard cell specific promoter of potato (DE 42 07358 A1) for the tapetum specific promoter TA29 from tobacco (EP 0 344 029 B1) and for the pistil and pollen specific SLG promoter from *brassica* (Dzelzkàlns et al., 1993).

From sugar beet, an organ specific promoter is known, which is mainly active in the storage root tissue of sugar beet (WO 97/32027). However, this promoter of the sucrose synthase gene is not only active in roots but also, with less activity, in other tissues like leaves (Hesse and Willmitzer, 1996).

SUMMARY OF THE INVENTION

Therefore, it is the problem of the present invention to provide new promoters and plants with the possibility of tissue specific expression of genes either in roots or in above-ground plant parts.

This problem is solved according to the invention by promoters according to the main claim and a transgenetic plant obtainable by transformation of a plant cell with a promoter according to the main claim, which is operatively linked to a transferred gene, and subsequent regeneration of the transgenetic plant.

Some of the terms used in this application are specified below:

The term promoter refers to a nucleotide sequence, which regulates the expression of a gene under its control, if necessary in dependency of endogenous and exogenous factors. Among these factors are, e.g. inductors, repressors and similar DNA binding proteins as well as environmental influences. A promoter may consist of several elements. However, it at least comprises one regulatory element, which is responsible for the transcription of the gene under its control.

A promoter, which is active in above-ground and chloroplast containing plant parts, as leaves, and not in below-ground organs, shows a detectable activity in leaves, measured by RNA blots, which, under comparable experimental conditions, is detectible in below-ground organs of the plant to less than 20%, preferably to less than 10% and more preferably to less than 5%. This specificity is not restricted to a particular experimental time point, but is generally present during the entire vegetation period.

A promoter, which is active in below-ground organs and not in above organs of the plant, for example shows in roots at detectable activity measured by RNA blots, which is, under comparable experimental conditions, detectable in above-ground organs of the plant like petioles, leaves and blossoms to less than 20%, preferably to less than 10% and more preferably to less than 5%. This specificity is not restricted to a particular experimental time point, but is generally present during the entire vegetation period.

"Derivatives" of a promoter are shortened or elongated or sectionwise identical versions of this promoter or homologes with the same, modified or singular characteristics.

"Inducible by pathogens" means the action of external factors on the plant, which result in a defence reaction of the plant. These can be attacks of insects (bites), bacteria, fungi, nematodes or other pathogens, but also abiotic influences as mechanical wounding (e.g. by hail-storm).

"Direct antifungal activity" means that gene products act directly antifungal by, e.g. dissolving cell walls or by coding for phytoalexine synthases and metabolites, respectively, which inhibit the fungal metabolism.

"Indirect antifungal activity" means, that gene products activate the plant gene defense. Among these genes are, e.g. resistant genes, components of signal transduction (as kinases, phosphatases), transcription factors or enzymes, which produce signal substances (as enzymes forming ethylene, salicylic acid or jasmonate, enzymes forming reactive oxygen species, enzymes forming nitrogen monoxide).

"Sink leaves" are such leaves, which, due to their small size, consume more carbohydrates than they produce themselves.

"Source leaves" are leaves, which, due to their size, produce more carbohydrate then they consume themselves.

By "infection" is meant the earliest time point, at which the metabolism of the fungus (the growth of the fungus) is prepared for a penetration of the host tissue. Among these are, e.g. the growth of hypha or the formation of specific infection structures, as penetration hypha and appressoria.

The expression "homology" hereby means a homology of at least 70% on DNA basis, which can be determined according to known methods, e.g. computer assisted sequence comparisons (S. F. Altschul et al. (1990), Basic Local Alignment search tool, J. Mol. Biol. 215: 403-410).

Complementary nucleotide sequence means with respect to a double-stranded DNA that the second DNA strand, which is complementary to the first DNA strand, comprises the nucleotide bases, which correspond to the bases of the first strand according to the rules for base pairing.

The term "hybridizing" as it is used herein means hybridizing under conventional conditions, as they are described in Sambrook et al. (Molecular Cloning. A laboratory manual, Cold Spring Harbor Laboratory Press, $2^{nd}$ edition, 1989), preferably under stringent conditions. Stringent hybridization conditions are for example: hybridizing in 4×SSC at 65° C. and sub-sequent multiple washing in 0.1×SSC at 65° C. for a total of 1 hour. Less stringent hybridization conditions are for example: hybridizing in 4×SSC at 37° and subsequent multiple washing in 1×SSC at room temperature. The term "stringent hybridization conditions" as used herein can also mean: hybridizing at 68° C. in 0.25 M sodium phosphate, pH 7.2, 7% SDS, 1 mM EDTA and 1% BSA for 16 hours and subsequent washing twice with 2×SSC and 0.1% SDS at 68° C.

In the following, the invention is described in more detail, referring to the figures and examples.

The promoters and their derivatives according to the invention are particularly characterized by the fact that they are exclusively active in roots or in above-ground organs of a plant. With their help, transgenetic plants with particular characteristics can be produced. In a preferred manner, they can be used for the following purposes:
a. amendment of the carbohydrate metabolism
b. avoidance of storage substances losses
c. expression of an invertase inhibitor
d. expression of a fructosyl transferase
e. expression of a levan sucrase
f. expression of genes coding for transporter proteins for N-compounds
g. development of features, which increase the resistance/ tolerance towards pathogens.

The promoters according to SEQ ID NO: 1 and SEQ ID NO:2 are active in roots, in particular of sugar beet, but not in above-ground organs of this plant. This characteristic can be used for the improvement of the metabolism of transgenetic plants, in particular the carbohydrate metabolism of sugar beets. It is an improvement of the carbohydrate metabolism to reduce the loss of sucrose and the accumulation of glucose and fructose during the storage of beet bodies after harvest. The use of an invertase inhibitor gene under the expression control of SEQ ID NO: 1 and SEQ ID NO: 2 can reduce the activity of vacuolar invertase in the root. By organ specific expression of the inhibitor, pleiotropic effects are avoided, which inhibit the invertase in the entire plant.

Further improvements of the carbohydrate metabolism are the production of the sweetener palatinite or the synthesis of polyfructanes in the root of sugar beets under the use of the described sequences.

The root specific active promoters (SEQ ID NO: 1 and SEQ ID NO: 2) can also be used to improve the nitrogen metabolism of the plants. For this, transport protein genes for ammonium ($NH_4^+$), nitrate ($NO_3^-$) and nitrite ($NO_2^-$) ions are overexpressed in the root, and the uptake of the mentioned ions is increased. A further improvement of the N-metabolism is the reduced incorporation of "bad nitrogen" in the storage organs of the plant. Elevated concentrations of N-compounds in storage organs often reduce the nutrition physiological value of harvest products or hamper the isolation of storage substances, as sucrose, from sugar beet roots. A reduced incorporation of "bad nitrogen" in the root can be achieved by a reduced uptake of ammonium and nitrate ions from the soil. For this purpose root specific active promoters are used, in order to reduce the expression of endogenous transporter genes organ specifically by, e.g. an "anti-sense" approach.

The promoters according to the invention can also be used to improve the resistance to diseases of the plants.

Viral infections of the sugar beet are often restricted to only one organ as the root or the above-ground plant parts. Thus, the virus BNYVV infects and colonizes primarily the beet root, and yellowing viruses BMYV and BYV are found only in leaves. Root active promoters and promoters, which are only active in above-ground organs can be used to obtain organ specificity via the virus resistance concepts, which are based on gene silencing and anti-sense technique, respectively.

SEQUENCES AND FIGURES

The nucleotide sequences of SEQ ID NO: 1, SEQ ID NO: 2, SEQ ID NO: 3 and SEQ ID NO: 4 are depicted in 5'-3'-orientation.

BRIEF DESCRIPTION OF THE DRAWINGS

On the basis of the restriction analyzes, which have been carried out.

3046 of nucleotide sequence SEQ ID NO: 4. The restriction enzymes in brackets cut the plasmid several times.

Figure 11:
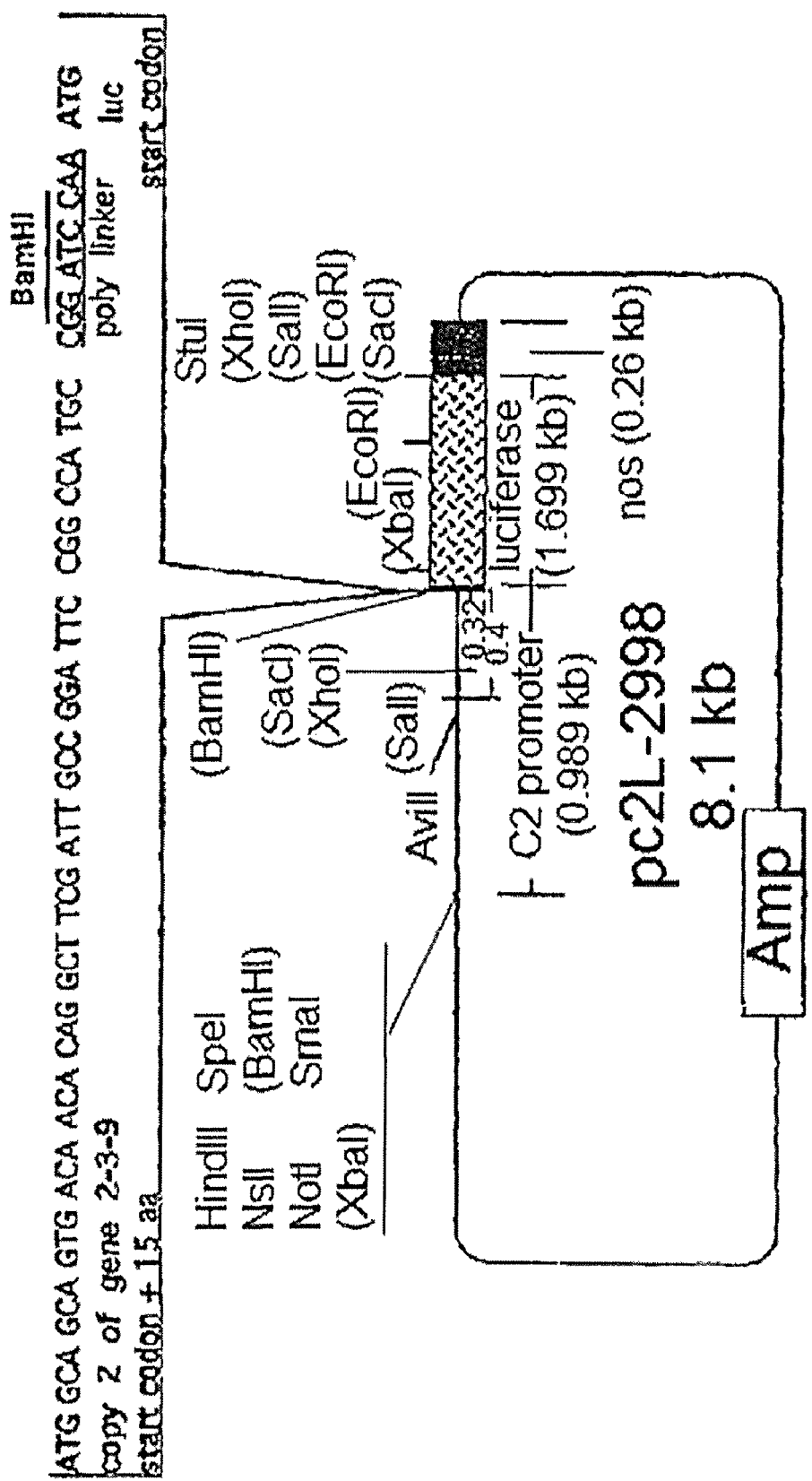

FIG. 11 shows the 6.04 kb reporter gene construct pc2L-989. The vector pc2L-989 is formed by a 5'-deletion of the C2 promoter of plasmid pc2L-2998. The C2 promoter in vector pc2L-989 comprises the nucleotide positions 2011-3046 of nucleotide sequence SEQ ID NO: 4. The restriction enzymes in brackets cut the plasmid several times.

Figure 12:
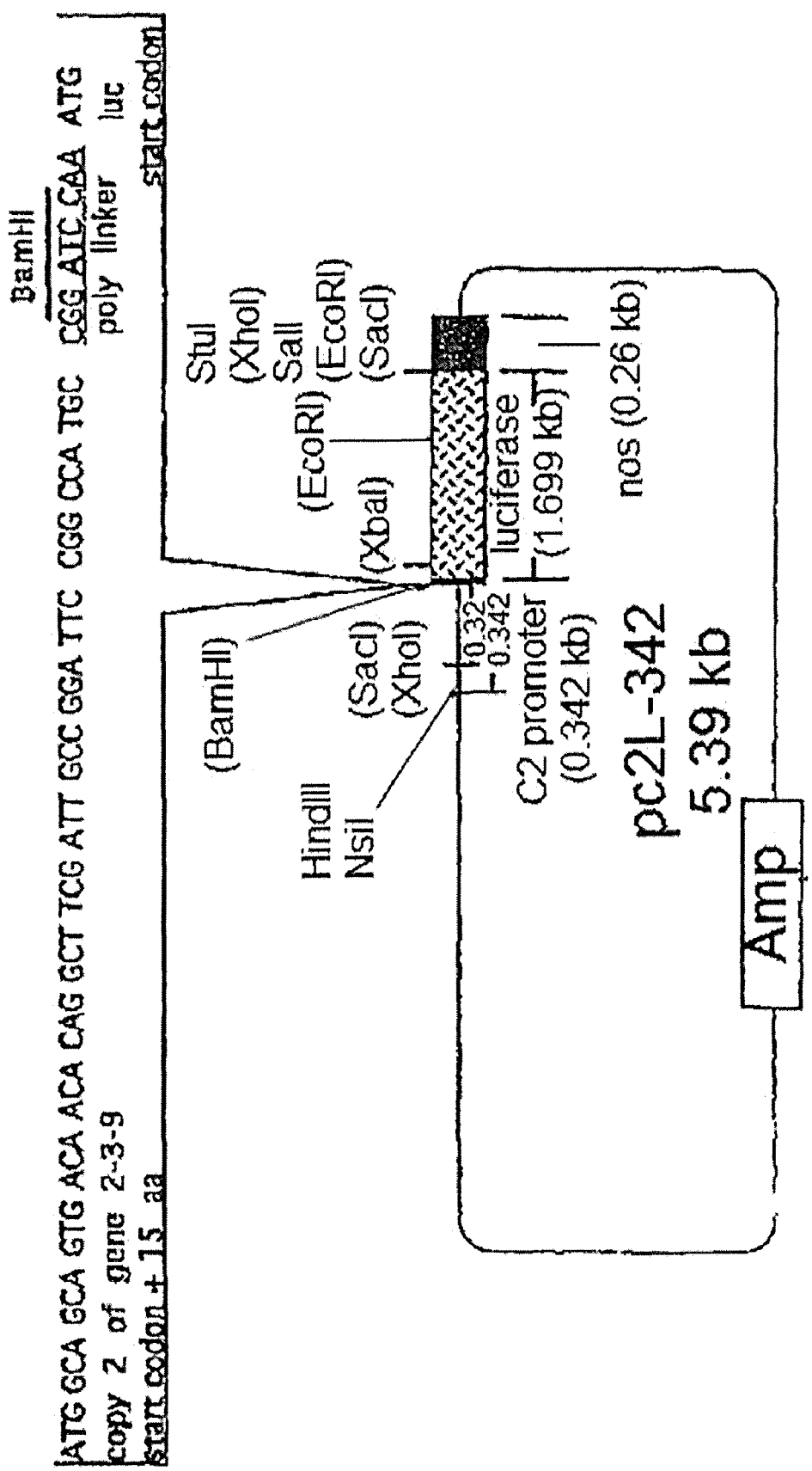

FIG. 12 shows the 5.39 kb reporter gene construct pc2L-342. The vector pc2L-342 is formed by a 5'-deletion of the C2 promoter of plasmid pc2L-2998. The C2 promoter in vector pc2L-342 comprises the nucleotide positions 2657-3046 of nucleotide sequence SEQ ID NO: 4. The restriction enzymes in brackets cut the plasmid several times.

FIG. 13 shows the activity of reporter gene constructs pc2L-2998, pc2L-1827, pc2L-989 and pc2L-342 after ballistic transformation in sugar beet leaves. Per construct 1-2 DNA preparations, each with 4 experimental repeats were used. The calculated *Photinus pyralis* luciferase activities were normalized by parallel measurement of *Renilla reniformis* luciferase activity, and variations in the transformation efficiency were thereby compensated.

Figure 14:
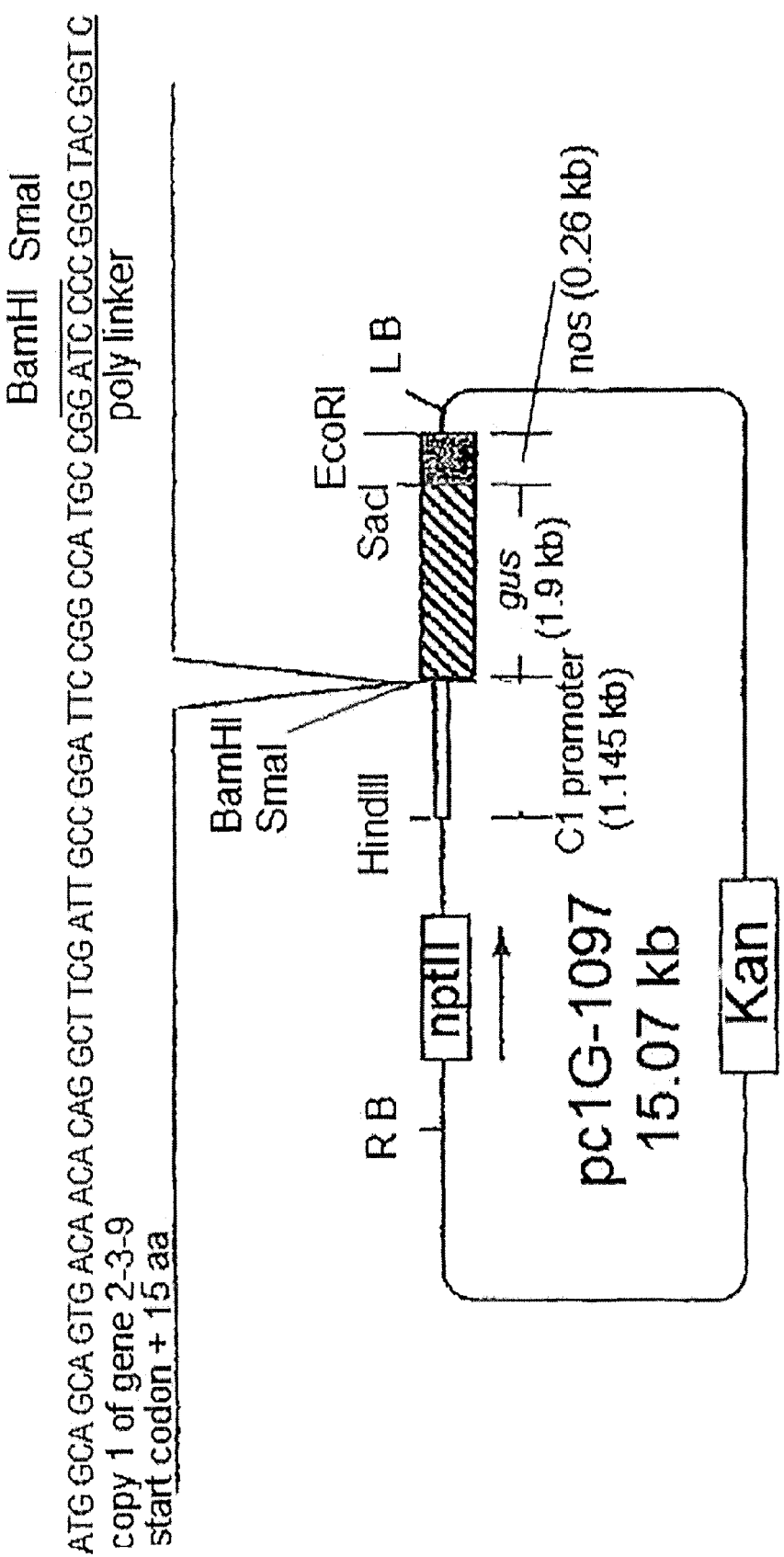

FIG. 14 shows the 15.07 kb binary plant transformation vector pc1G-1097. The C1 promoter is translationally fused with the gus reporter gene. The C1 promoter comprises the nucleotide positions 1-1145 of the nucleotide sequence of SEQ ID NO:3.

Figure 15:
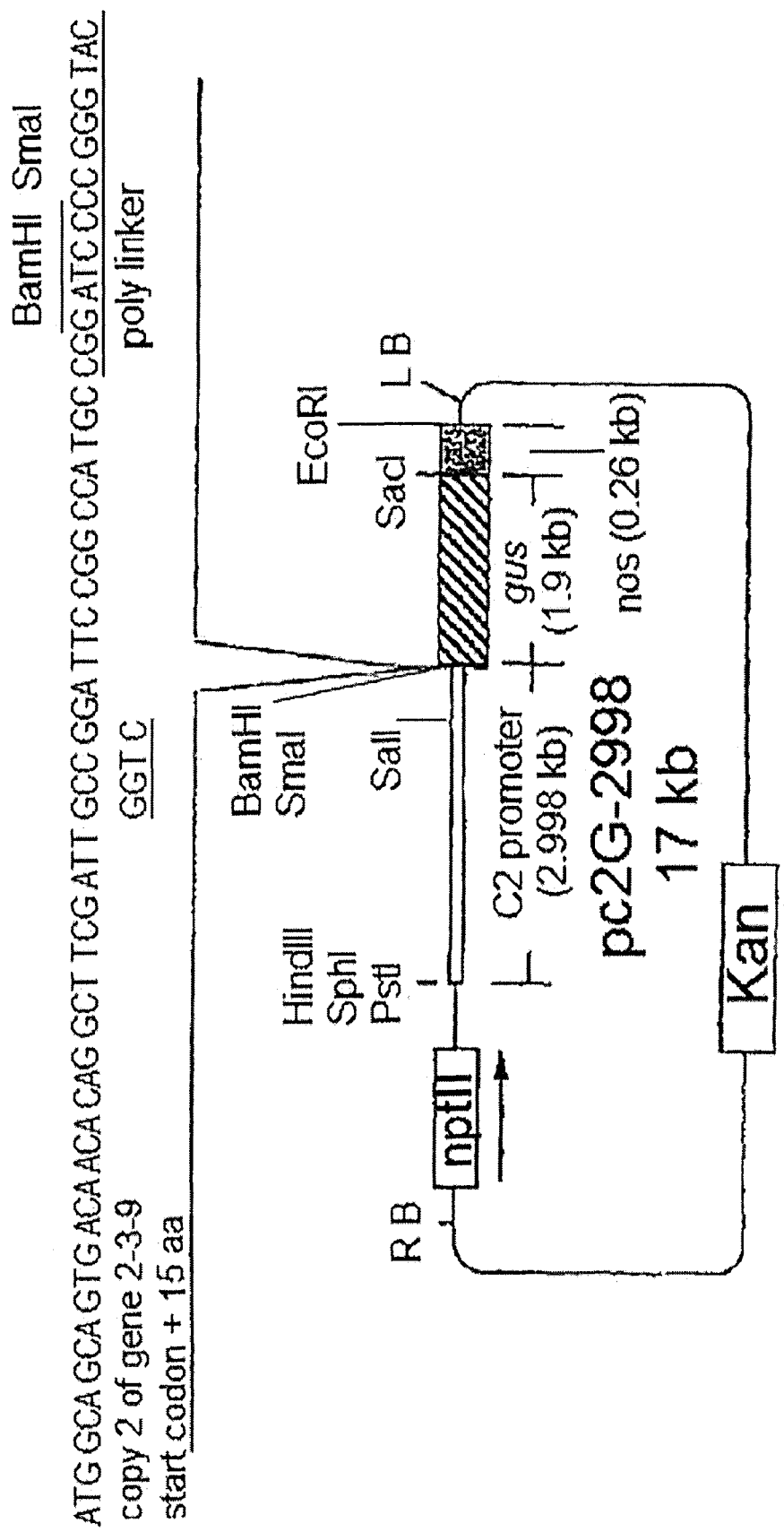

FIG. 15 shows the 17 kb binary plant transformation vector pc2G-2998. The C2 promoter is translationally fused with the gus reporter gene. The C2 promoter comprises the nucleotide positions 1-3046 of the nucleotide sequence of SEQ ID NO: 4.

Figure 16:
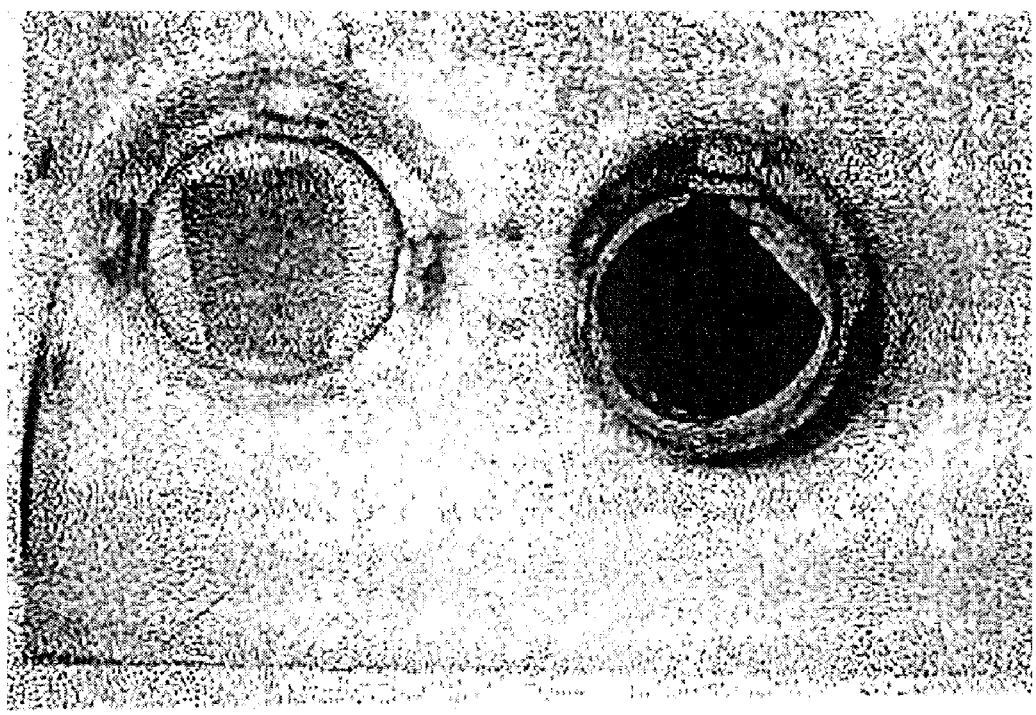

FIG. 16 shows the histochemical detection of the activity of the C1 promoter in leaves of transgenetic *brassica* plants. Leaf pieces of the transformant pc1G-1097-86 (right) are colored in blue due to gus reporter gene activity, in comparison to the non-transgenetic control (left).

Figure 17:
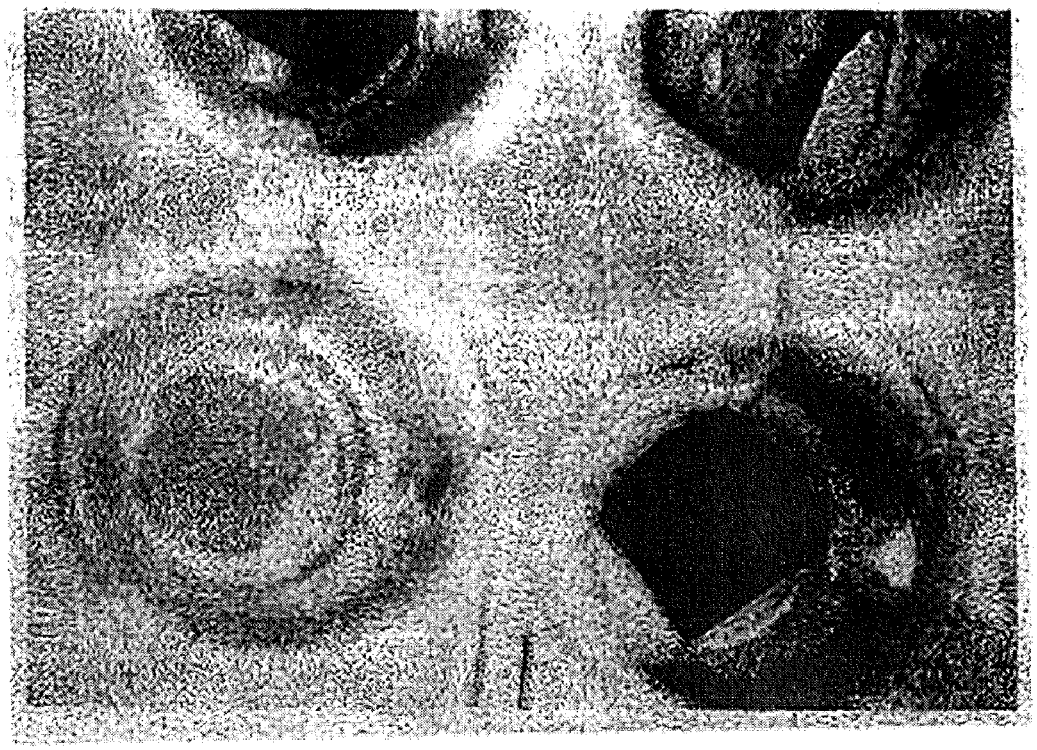

FIG. 17 shows the histochemical detection of the activity of the C1 promoter in leaves of transgenetic tobacco plants. A leaf piece of the transformant pc1G-1097-3 (right) is colored in blue due to gus reporter gene activity, in comparison to the non-transgenetic control (left).

Figure 18:
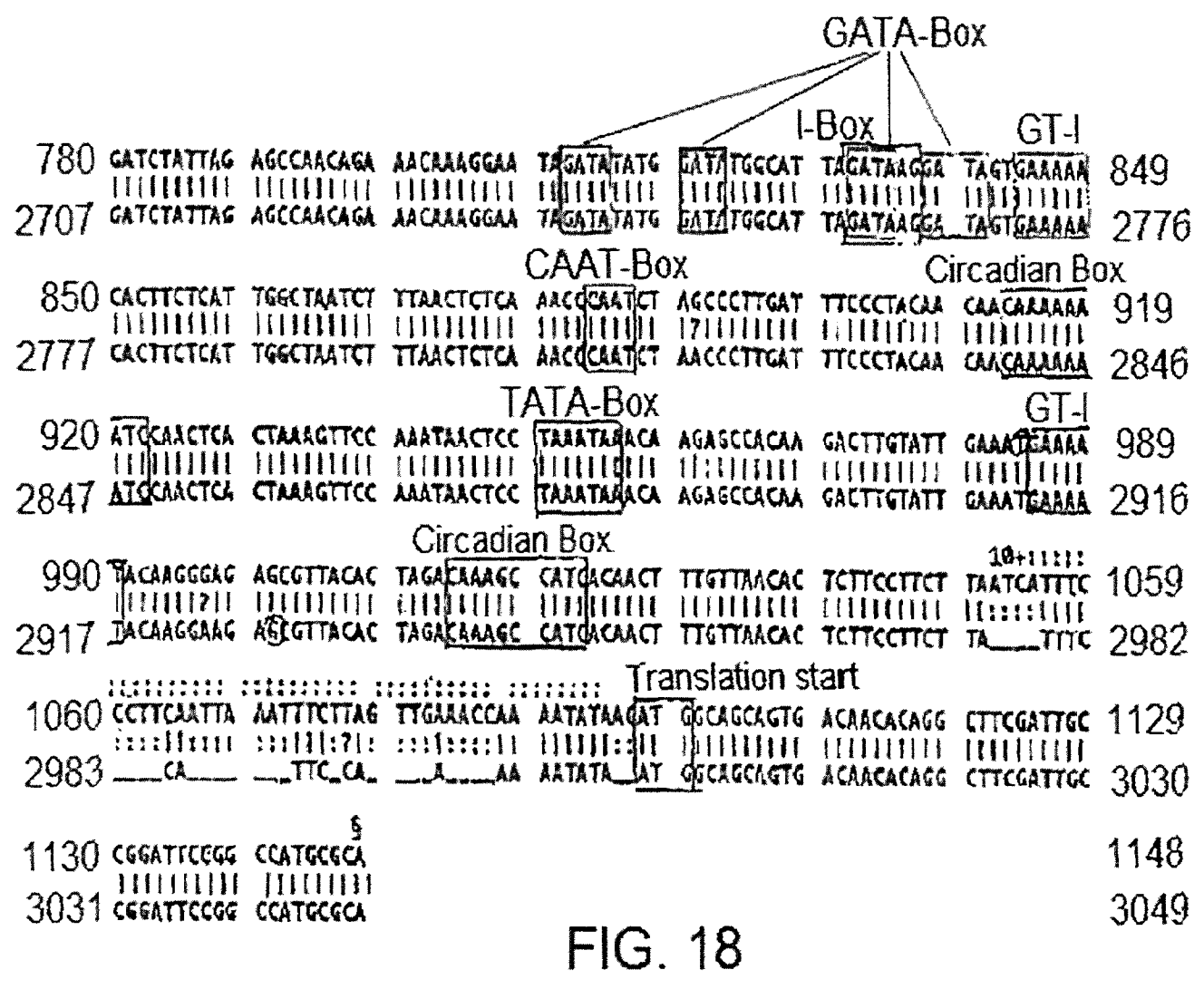

FIG. 18 shows a DNA sequence comparison between the conserved regions of the C1 and the C2 promoter. In the figure, the positions of GATA boxes, I box, GT-1 binding sites, CAAT box, two circadian boxes and TATA boxes are indicated. The translational start of the first copy of gene 2-3-9 is at position 1098, and the translational start of the second copy of gene 2-3-9 is at position 2998. The transcription initiation point within the C1 promoter is at position 984, and the transcription initiation point within the C2 promoter is at position 2928.

EXAMPLES

Isolation of Root and Leaf Specific Expressed cDNAs of Sugar Beet

According to the method of suppression subtractive hybridization (Diatchenko et al., 1996) an accumulation of cDNA fragments of genes expressed in leaves and the taproot of sugar beet was conducted. For this, from both tissues first total RNA and then polyA(+) RNA was isolated. Additionally, total RNAs from sprouts and inflorescences were isolated, which were used for Northern blot analysis.

The following experiments were carried out according to the protocol of the PCR select systems of the company CLONTECH. With polyA(+) RNA from leaf and taproot, cDNA was synthesized. With both cDNAs two subtractions were carried out. For the accumulation of leaf specific genes, the leaf cDNA as a probe was subtracted against the cDNA from taproot. For the accumulation of taproot specific genes, the cDNA from taproot as a probe was subtracted against the cDNA from leaf. The subtraction was carried out precisely according to the protocol of the CLONTECH kit, and also the internal control was carried out. All further molecular biology experiments were carried out according to standard protocols (Sambrook et al., 1989). After subtraction, amplified cDNA fragments were obtained, which were either accumulated with leaf or root specific genes.

For further analysis, the cDNA fragments were cloned into the TA cloning vector pCR2.1 (invitrogen) and transformed into *E. coli*. A blue-white selection allowed the identification of recombinant plasmids (Sambrook et al., 1989). In white colonies, the expression of β-galactosidase is suppressed by an insert, which leads to white colonies, because the enzyme substrate, which is added to the medium is no longer cleaved. Per μg of PCR product, approximately 300 white colonies were obtained. In total, 62 clones of the subtraction of taproot specific genes and 60 clones of the subtraction of leaf specific genes were further characterized. For this, the DNA of the clones was cleaved with the restriction enzyme RsaI. This isolated the inserts from adaptors. Then, half of the cleaved DNA was electrophoretically separated on gels, and the DNA was transferred to nylon membranes. For the identification of DNA fragments, which were specifically accumulated, the filters with the PCR products (cDNA fragments) were hybridized with both subtractions. cDNA fragments, which hybridized with the cDNA fragments from which they were subcloned but not or not as strong with the cDNA fragments from the other subtraction were further analyzed, because they represented potentially accumulated or tissue specific genes.

Among 62 clones from the subtraction of taproot specific genes, 18 were identified, which hybridized strongly with the cDNA fragments of the subtraction of taproot specific genes but not or only weakly with the cDNA fragments of the subtraction of leaf specific genes. Among 60 clones from the subtraction of leaf specific genes, 23 were identified, which hybridized strongly with the cDNA fragments of the subtraction of leaf specific genes but not or only weakly with the cDNA fragments of the subtraction of taproot specific genes. All identified cDNA inserts of both subtractions were entirely sequenced, and compared to each other with a sequence analysis program (Pileup, GCG Wisconsin Analysis Package). Based on similarities (homologous) of the sequences among each other, in total 9 different cDNA fragments of the subtraction of taproot specific genes and 14 different cDNA fragments of the subtraction of leaf specific genes remained.

All 9 different cDNA fragments of the subtraction of taproot specific genes and 7 of 14 different cDNA fragments of the subtraction of leaf specific genes were hybridized by Northern blot analysis with RNA from leaf, taproot, sprout and inflorescence. Three clones, 2-1-36, 2-1-48 and 2-3-9 showed a very specific hybridization pattern. 2-1-36 and 2-1-48 hybridized only with RNA from taproot and not with RNA from leaf, sprout and inflorescence, and 2-3-9 hybridized only with RNA from green tissue and not with RNA from taproot.

Genes 2-1-36 and 2-1-48 are Expressed Exclusively in the Sugar Beet Root During the Vegetation Period In order to analyze the expression behavior of genes 2-1-36 and 2-1-48 during the entire vegetation period, sugar beet seeds are applied to the field. During the central European vegetation period 5, complete sugar beet plants are harvested after 4, 6, 10, 12, 16 and 22 week, respectively after sowings. The plants show at no time signs for diseases. Total cell RNA is isolated according to Logemann et al., 1987 from the organs sink and source leaf, petiole, lateral root and taproot (root body). The expression of the genes is determined by RNA blot analyses.

For the analyses of development dependent gene expression with an RNA blot, 10 µg total cell RNA per organ and time point are separated in a denaturated formaldehyde agarose gel, as described in Sambrook et al., (1989). Electrophoretically separated RNA is transferred by capillar blot technique (Sambrook et al., 1989) onto a hybond N nylon membrane (Amersham Pharmacia Biotech, Freiburg). Radioactive labeling of 20 ng of 2-1-36 and 2-1-48 cDNA fragments with 50 µCi $^{32}$P-dATP (6000 Ci/mMol, Amersham Pharmacia Biotech, Freiburg), respectively, is carried out with the help of Prime-It II random primer kit (Stratagene GmbH, Heidelberg) according to the manufacturer's instructions. The subsequent hybridization of the RNA filter with labeled probe is carried out in 20 ml hybridization buffer (50% formamide, 5×SSC, 5×Denhard's, 1% SDS, 0.1 mg herring sperm DNA, 40 mM sodium phosphate puffer pH 6.8) at 42° C. in a hybridization oven (Biometra GmbH, Goettingen) according to Sambrook et al., 1989. After hybridization, the nylon membrane is washed and exposed on an X-ray film (Kodak BioMax MS, Kodak AG, Stuttgart) in the presence of an intensifying screen (Kodak BioMax MS, Intensifying Screen, Kodak AG, Stuttgart) for 6-24 h at −80° C. The development of the X-ray film is then done in X-ray film developer and X-ray film fixer (Tetenal Photowerk GmbH and Co., Norderstedt).

Figure 1:
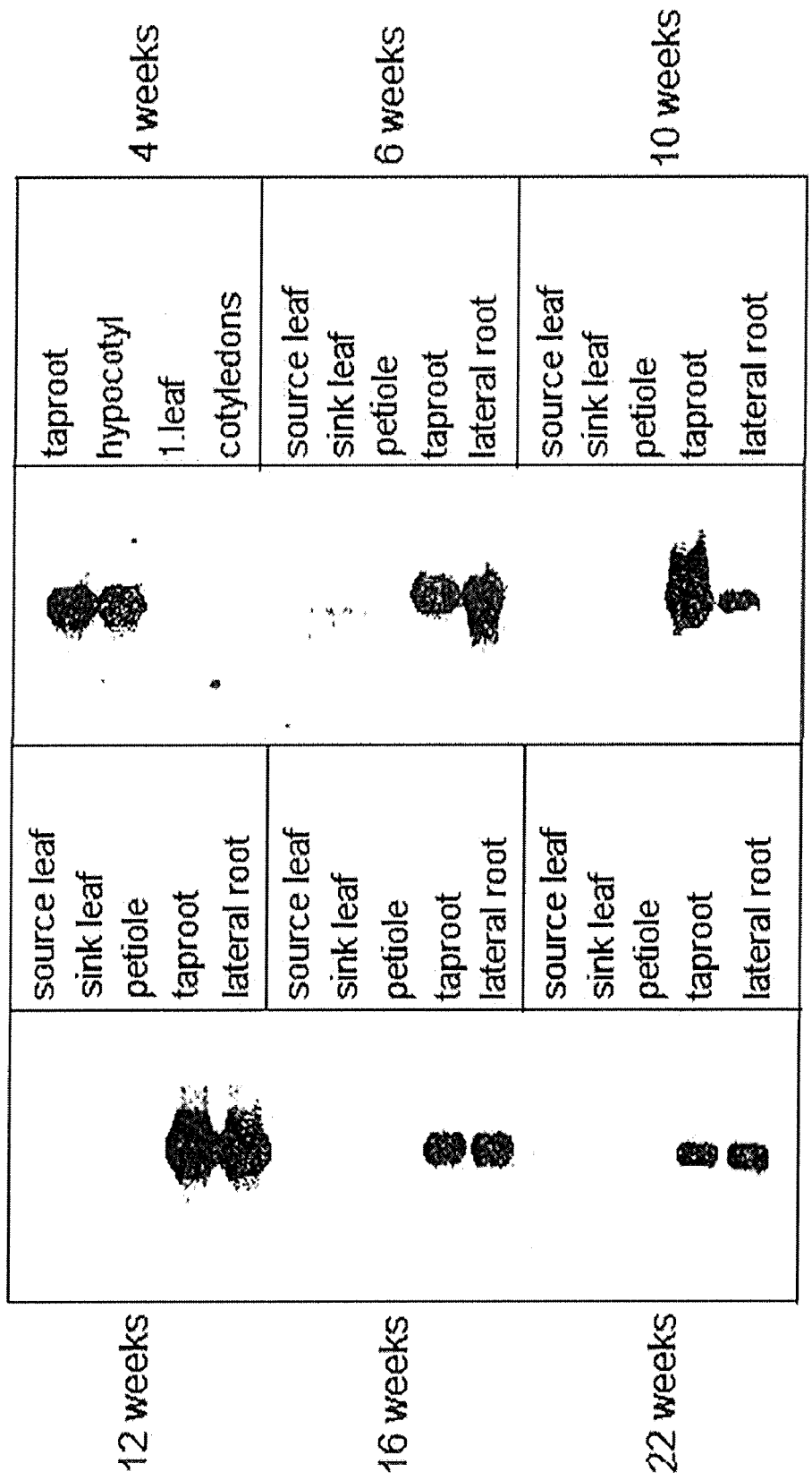
FIGS. 1 and 2 show exclusively root specific expression of gene 2-1-48 and 2-1-36 during root development by a RNA blot experiment. 10 μg total cell RNA, which had been isolated from different organs of 4, 6, 10, 12, 16 and 22 week old sugar beets, respectively, was separated in a denaturated formaldehyde agarose gel. RNA was isolated from the taproot, the lateral roots, sink and source leaves and, in case of 4 week old plants, from the hypocotyl and the seed leaves. The cDNA fragment 2-1-48 and 2-1-36, respectively, was used as hybridization probe.

The RNA blot hybridized with probe 2-1-48 shows that the gene 2-1-48 in 4 week old sugar beet is only expressed in the root and in the rooted head (hypocotyl) and in 6, 10, 12, 16 and 22 week old sugar beet exclusively in the taproot and the lateral roots (FIG. 1). At no time point an expression of gene 2-1-48 can be observed in the above-ground plant organs petiole, source and sink leaf.

The RNA blot was evaluated with the help of a phosphoimager (Bioimaging Analyzer BAS 1000, Fujiy Japan), in order to quantify the transcript accumulation. The data of the quantification are depicted in table 1.

The accumulation of a transcript, which is detectable by probe 2-1-48 and thus a corresponding promoter activity is strongly expressed in taproots of 4, 6 and 10 week old plants. In 12 week old roots, the gene expression reaches its maximum and then decreases significantly in 16 and 22 week old plants. Therefore, the gene 2-1-48 is strongly and very strongly expressed in root bodies of young beets and plants of middle age, respectively, and significantly decreases with increasing age. In the above-ground plant organs it is only possible to detected a very weak gene expression in petioles and leaves in young beets. The detectable transcript amount in 6, 10 and 12 week old petioles is only 3, 2 and 1.2%, respectively of the transcript amount detectable in the taproot at these time points. The detected transcript amount in 6 and 10 week old sink and source leaves is 2.5% and 1.6 and 2.1%, respectively of the accumulated 2-1-48 transcripts in the taproot at these time points.

Figure 2:
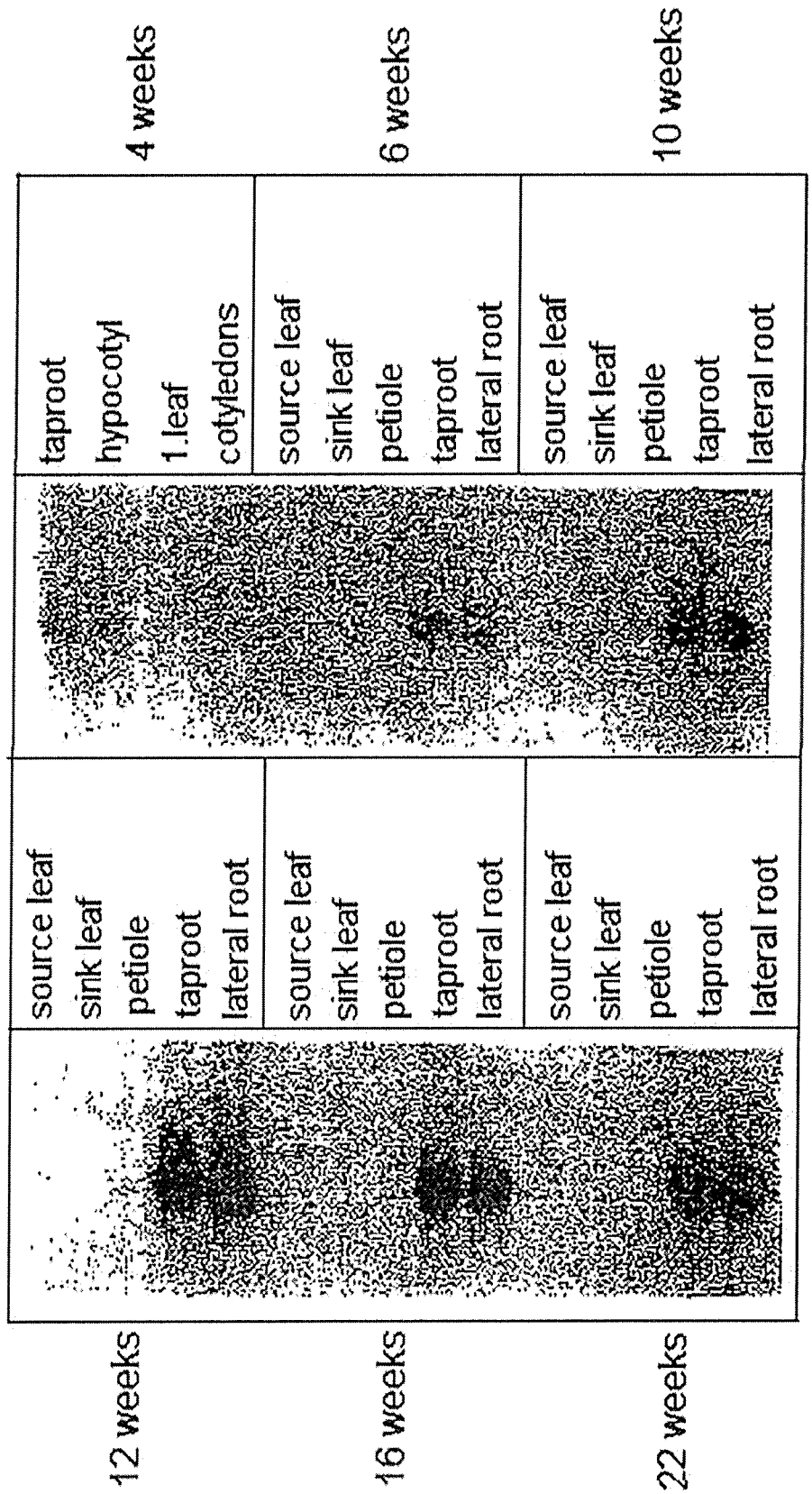

The use of the cDNA clone 2-1-36 as hybridizing probe for the development specific RNA blot shows that the gene is expressed in 4 week old sugar beets only in the root and the rooted head (hypocotyl) and in 6, 10, 12, 16 and 22 week old plants exclusively in the taproot and in the lateral roots (FIG. 2). In the above-ground organs petiole, sink and source leaf, a transcript is at no time point visible. The expression of gene 2-1-36 is not constitutive in the root and the lateral roots but development dependent. This tendency is already visible on the autoradiogram of the RNA blot, but is even more pronounced after the quantification of the labeled filter by the phosphoimager (table 2). While gene 2-1-36 is expressed during the juvenile development of the beet in 4, 6 and 10 week old taproots and 6 and 10 week old lateral roots weakly but increasingly stronger, beets and lateral roots show a very strong increase of expression after 12 weeks. The expression of gene 2-1-36 decreases slightly in taproots at the time points 16 and 22 weeks in comparison to the 12 week value, but it remains on a high level. In lateral roots of 16 week old plants, there is also a decrease of 2-1-36 expression in comparison to the 12 weeks value. However, the expression of 2-1-36 in this organ increases in 22 week old plants again to the high 12 week level. Therefore, the gene 2-1-36 is expressed weakly in 4-10 week old plants and is expressed strongly and therefore development dependent in 12-22 week old plants. In the above-ground organs sink and source leaf and petiole, a significant transcript amount cannot be quantified at any time point. All measured values in these organs are in the range of background.

Gene 2-3-9 is Exclusively Expression in Above-Ground Plant Organs During Beet Development In order to analyze the expression of gene 2-3-9 during the entire vegetation period, the RNA blots for the expression analysis of root specific expressed genes were hybridized with probe 2-3-9. These RNA blots were prepared using RNA of the organs sink and source leaf, petiole, taproot and lateral root of 4, 6, 10, 12, 16 and 22 week old sugar beets, as described.

Figure 3:
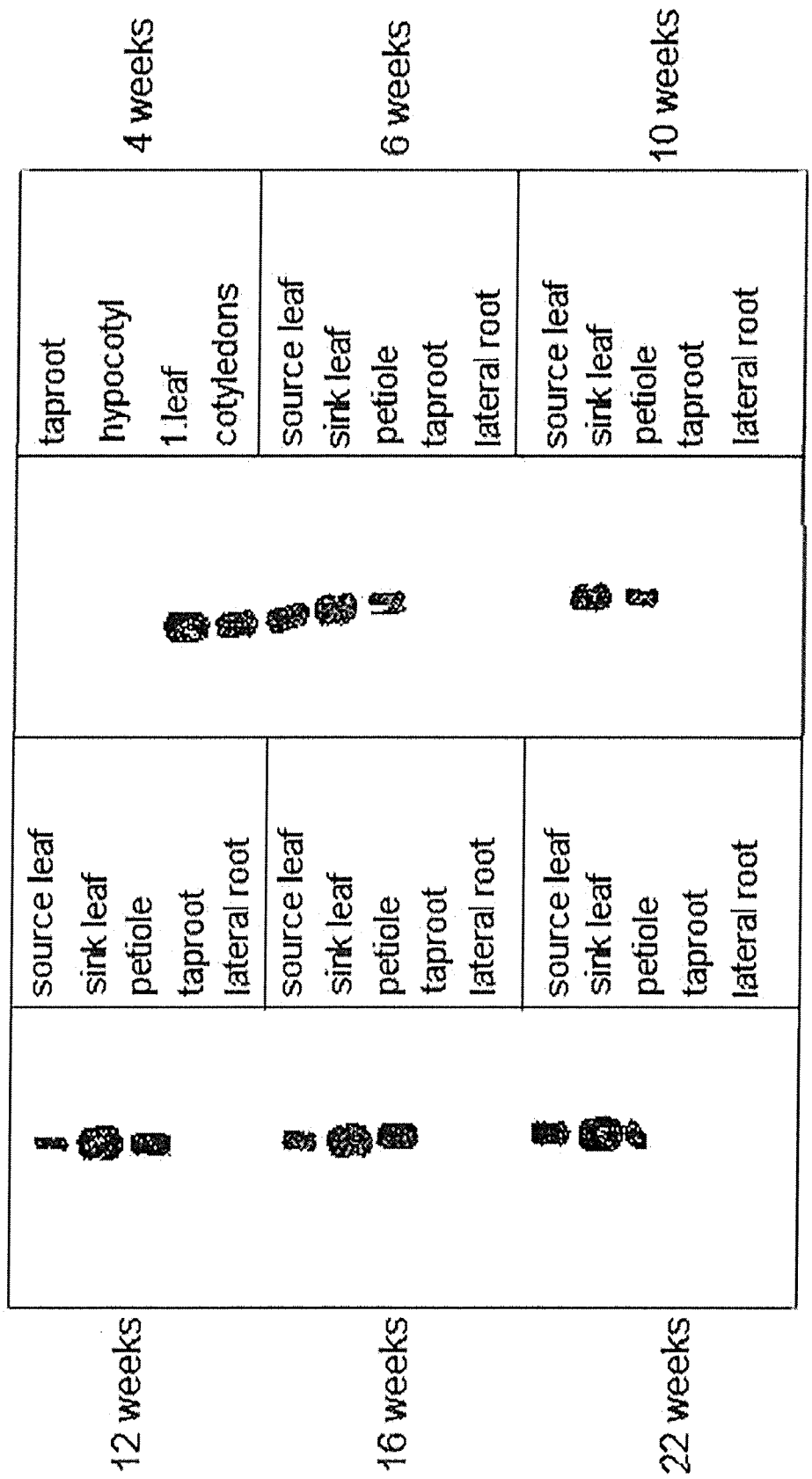
FIG. 3 shows by an RNA blot experiment, that gene 2-3-9 is expressed during the beet development exclusively in above-ground plant organs. 10 μg total cell RNA, which had been isolated from different organs of 4, 6, 10, 12, 16 and 22 week old sugar beets, respectively, were separated in a denaturated formaldehyde agarose gel. RNA was isolated from the taproot, the lateral roots, sink and source leaves and, in the case of 4 week old plants, from the hypocotyl and the seed leaves. The cDNA fragment 2-3-9 was used as hybridization probe.

The hybridization result of the RNA blot shows, as depicted in FIG. 3, that gene 2-3-9 is expressed at any analysis time point in sink and source leaves and petioles. An expression in the below-ground plant organs lateral and taproot is at no time point optically visible. Quantification of the RNA blot with the help of a phosphoimager confirms the optical impression and shows the absence of 2-3-9 transcripts in taproots and lateral roots and a strong transcript accumulation in leaves and petioles (table 3). The measured values for the taproot and lateral root are calculated to zero and are in the region of variation of the background. Therefore, gene 2-3-9 is exclusively expressed in above-ground plant parts during the entire vegetation period.

Gene 2-3-9 is Present in Different Copy Numbers in Different Sugar Beet Genotypes The number of genomic copies of gene 2-3-9 is determined for both sugar beet genotypes 1K0088 and 4B5421. Genomic DNA is isolated from the leaves of both genotypes according to Saghai-Maroof et al., (1984). Each 10 µg genomic DNA is individually cleaved by restriction enzymes EcoRI, HindIII, PstI, SalI, BamHI, EcoRV, XhoI and BglII, and the resulting DNA fragments are separated in a 0.8% agarose gel. The DNA fragments are transferred by alkaline transfer to a hybond N nylon membrane (Amersham Pharmacia Biotech, Freiburg). Radioactive labeling of 20 ng of the cDNA fragment 2-3-9 with 50 µCi $^{32}$P-dATP (6000 Ci/mMol, Amersham Pharmacia Biotech, Freiburg) and hybridization is exactly done as described for RNA blots. After hybridization, the nylon membrane is exposed on a X-ray film (Kodak BioMax MS, Kodak AG, Stuttgart) in the presence of an intensifying screen (Kodak BioMax MS Intensifying Screen, Kodak AG, Stuttgart) for 16 h at −80° C., and the X-ray film is subsequently developed.

Figure 4:
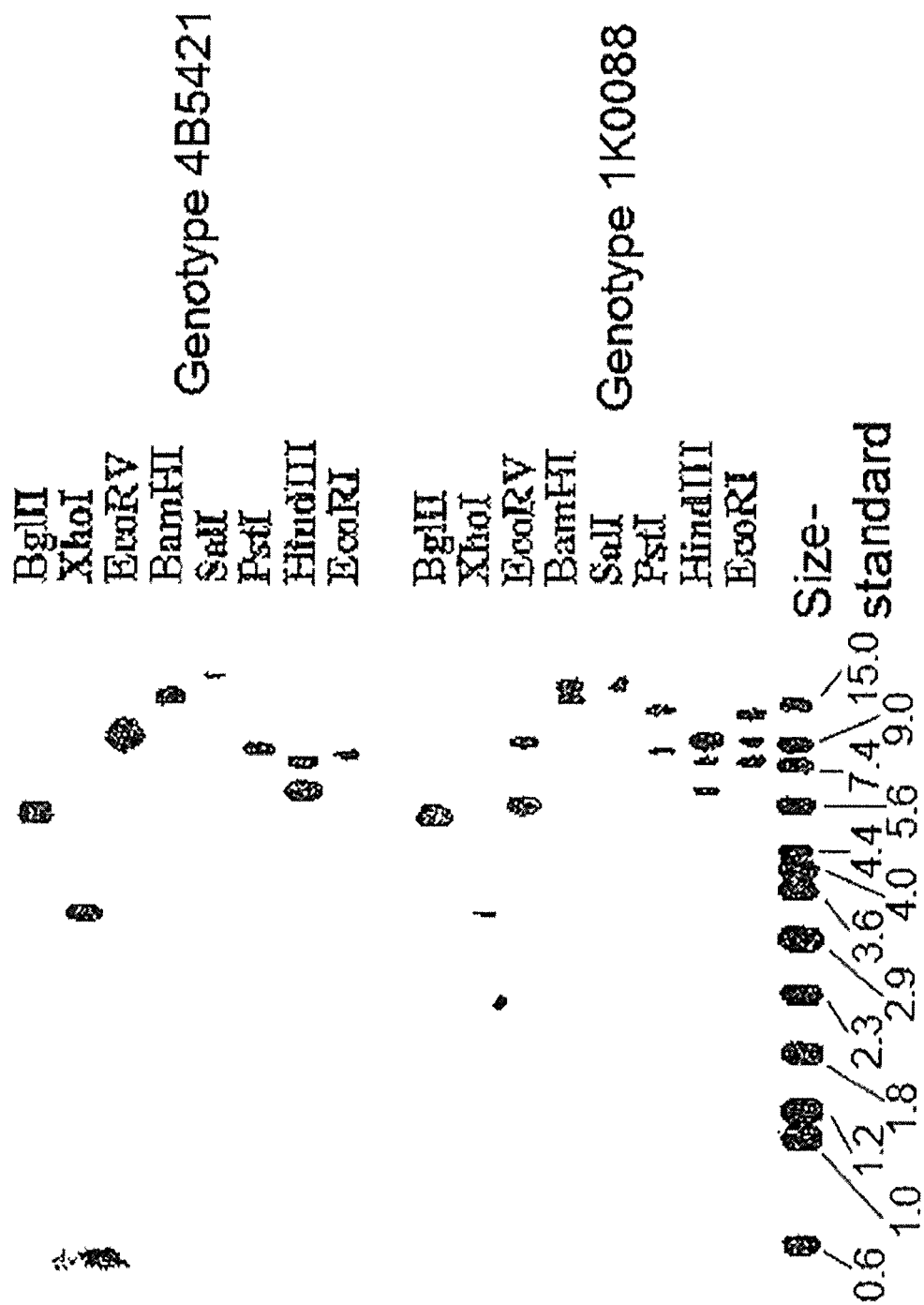
FIG. 4 shows in a DNA blot experiment that in the genome of sugar beet genotypes 1K0088 two copies of the gene 2-3-9 and in genotype 4B5421 only one gene copy are/is present. 10 μg genomic DNA was used for restriction digest, respectively. The cDNA fragment 2-3-9 was used as hybridization probe.

The autoradiogram of the DNA blot shows that in the genome of genotype 1K0088 two copies of gene 2-3-9 are present, and that in genotype 4B5421 only one gene copy is present (FIG. 4). This estimation results from the observation that restriction digestion of the 1K0088 DNA with EcoRI and HindIII leads to three and with PstI to two hybridization signals, while under these conditions the DNA of 4B5421 leads to one signal with EcoRI and PstI and to two signals with HindIII.

Isolation of a Full-Length 2-1-48 cDNA Clone by RACE

Before genomic DNA fragments with the promoter region of gene 2-1-48 were identified, first a potentially full-length 2-1-48 cDNA was reconstructed. For this, the marathon cDNA amplification kit of CLONTECH was used. Marathon cDNA amplification is a method in order to conduct a 5' and 3' RACE (rapid amplification of cDNA ends) of one template. In total, six RACE products were sequenced for the 5' region and four RACE products were sequenced for the 3' region. By comparison of the sequences with each other and with the original cDNA fragment 2-1-48, a sequence for a potentially full-length cDNA fragment was reconstructed. The cDNA reconstructed from RACE products has an overall length of 841 base pairs and approximately corresponds to the length of the taproot specific transcript (approx. 800 bp), which was detected by Northern blot hybridization. The translation of all three possible reading frames led to a single unspaced reading frame of 150 amino acids. All other possible translation products comprised numerous stop codons. The 150 amino acids protein shows a homology to the 152 amino acid major latex protein homologue from *Mesembryanthemum crystallinum*. 66% of amino acids of both proteins (99 out of 149) are identical. The function of the protein is not known. The 5' ends of the cDNA clones of genes 2-1-36 and 2-3-9 were amplified by 5' RACE and isolated as described for gene 2-1-48.

Isolation of Promoters of Genes 2-1-48 and 2-1-36

The promoter regions in genomic clones of genes 2-1-48 and 2-36 were identified and subcloned. For this, clones of the sugar beet genotype 1K0088, which carry homologue sequences to the cDNA clones 2-1-48 and 2-1-36, were isolated from a genomic bank. The bank is established in lambda vector EMBL3 SP6/T7 and comprises genomic fragments with an average size of 20 kb. For cloning, the genomic DNA was partially cleaved with MboI and ligated into the BamHI restriction site of EMBL3. The inserts can be cleaved with XhoI. For the isolation of genomic clones, approx. 300,000 genomic clones were hybridized with cDNA fragments 2-1-48 and 2-1-36 in a plaque hybridization experiment (Sambrook et al., 1989). Hybridized phage plaques were picked and replated until only the corresponding hybridized phage clone was present in the probe. In total, thirteen clones were purified with the cDNA fragment 2-1-48, and 10 phage clones were purified with the cDNA fragment 2-1-36.

In these clones the genomic region 5' to the reconstructed full-length cDNA was then amplified and subcloned. For this, a restriction cleavage site for a restriction enzyme was searched in the cDNA, which is relatively close to the 5' end of the cDNA. For clone 2-1-48 a NcoI restriction site was identified, which is approx. 175 base pairs from the transcription initiation. The genomic clones, which were isolated with the cDNA fragment 2-1-48, were cleaved with XhoI and NcoI, separated gel electrophoretically and hybridized with an radio actively labeled oligonucleotide, which is 5' to the NcoI restriction site. This hybridization identified the NcoI/XhoI fragment, which comprised genomic sequences 5' to the reconstructed cDNA. These fragments were subcloned from three different lambda clones (L1, L12, L9) after fill-in of the ends with Klenow polymerase into a SmaI digested plasmid vector (pBluescript II SK). Bacterial colonies with recombinant plasmids were identified by colony hybridization. For each lambda clone three (L12-14, L12-15, L12-16, L-9-10, L-9-11, L-9-12) or two (L1-05, L1-06), recombinant plasmids were sequenced from both sites. At the ends of all clones the NcoI restriction site from the cDNA and the XhoI restriction site from the polylinker of the lambda vector were identified. The subcloned XhoI/NcoI inserts of the three lambda clones are approx. 7000 (L1), 4000 (L9) and 5000 (L12), respectively, base pairs long. The 4089 base pairs insert of the XhoI/NcoI fragment, which was used for subcloning, is depicted as SEQ ID NO: 1. The nucleotides 1-3967 comprise the entire regulatory 5' region of the gene and therefore the promoter 2-1-48. The transcribed, non-translated DNA sequence reaches from position 3911-3967 in comparison to the 5' end of full-length cDNA clone. The positions 3968-4089 correspond to the 5' end of the coding region. The DNA sequence present in plasmid L9 differs from the DNA sequence of SEQ ID NO:1 due to the cloning technique, so that the base pair at position 1 and 4089 is missing.

From the isolated DNA of the phages, which hybridizes with cDNA clone 2-1-36, a 1.923 kb NdeI-NdeI fragment, which comprises the promoter of the gene 2-1-36, was identified with the help of an oligonucleotide specific for the 5' region of the cDNA clone 2-1-36. The DNA ends of the NdeI-NdeI fragments were blunt ended by Klenow treatment, and the promoter was cloned in the vector pBluescript II SK, digested with the restriction enzyme SmaI. The nucleotide sequence of the subcloned fragment was determined. From the analyzed sequence 1919 by are depicted as SEQ ID NO: 2. The nucleotides 1-1840 comprise the entire subcloned regulatory 5' region of the gene and therefore the promoter 2-1-36. The transcribed non-translated DNA sequence reaches from position 1606-1840, in comparison to the 5' end of the full-length cDNA clone. The positions 1841-1919 are the first 79 translated base pairs of the gene.

Isolation of Promoters of Both Genes 2-3-9

The promoter regions of gene 2-3-9, which is present in two copies in the sugar beet genotype 1K0088, were identified and isolated. For this, lambda phages were isolated from the genomic bank of the genotype 1K0088, which inserts comprise a homology to the cDNA clone 2-3-9. In total, 300,000 phages of the bank constructed in vector EMBL 3 SP6/T7 were seeded according to the Lambda Library Protocol Handbook, Clontech, PT 1010-1 using *E. coli* strain K802 in melted LB top agarose+10 mM MgSO$_4$ on 150 mm petri dishes, which comprise LB medium+10 mM MgSO$_4$. The concentration of phages per plate was 25 000. In order to screen the seeded phages for promoters of gene 2-3-9, two replica of nylon filter (NEN Life Science Prodcuts, #NEF 978Y) per plate were prepared. For the hybridization experiment, the filters were hybridized with the radioactive labeled cDNA fragment 2-3-9. Twelve positive hybridized phages were picked with the help of a Pasteur pipette, isolated by corresponding microbiological dilution steps and purified until purity. The purity of the phage isolates was tested by radioactive hybridization after each step. DNA was isolated from 9 positive lambda phages by using the Qiagen lambda DNA preparation kit (Qiagen, Hilden, Germany). By combination of long distance PCR (LD-PCR) and restriction analysis, the location and the orientation of the coding region of gene 2-3-9 and thus of the promoter with respect to the left and the right phage arm was determined.

For the amplification of the cloned genomic fragments by LD-PCR, a primer combination was used, in which a commercially available 5' and 3' primer binds in the left and right phage arm, respectively, outside the cloned sugar beet DNA. The 5' and 3' primer of the "EMBL3 LD-Insert Screening Amplimer Set" (Clontech #9104-1, Heidelberg, Germany), which are phage arm specific comprise the nucleotide sequence CTG CTT CTA ATA GAG TCT TGC TGC AGA CAA ACT GCG CAA C (SEQ ID NO: 5) and TGA ACA CTC GTC CGA GAA TAA CGA GTG GAT CTG GGT C (SEQ ID NO: 6), respectively. The amplification of genomic sugar beet DNA fragments was carried out with the help of the "Advantage Genomic PCR Kit" (Clonetech #K1906-1, Heidelberg, Germany).

The PCR conditions, using 100 ng lambda DNA, a primer concentration of 0.4 µM, 0.5 µl Tth polymerase mix and 25 p. 1 reaction volume in a multicycler PTC-200 (MJ Research, Watertown, Mass., USA) were as follows:

| 1 x | Step 1: 1 min | 95° C. |
| 25 x | Step 2: 15 sec | 95° C. |
| | Step 3: 24 min | 68° C. |
| 1 x | Step 5: 10 min | 68° C. |

Further, for analytical purposes the 5' and 3' primer of the "EMBL3 LD-Insert Screening Amplimer Set" were used each in combination with primers S82 and S83, which are specific for the 5' and 3' portion of the coding region of gene 2-3-9. Thereby, the size of the genomic fragments adjacent to the reading frame could be determined. Primers S82 and S83 comprise the sequence AGG TTA TCA AAA GGC CCC TTT CCA GTC A (SEQ ID NO: 7) and GTT TGT GCA AGC CGA GCT GGT GAA CGC C (SEQ ID NO: 8). The PCR conditions correspond to the above-described LD-PCR conditions with a DNA amount reduced to 20 ng.

For restriction analysis of lambda clones with each 200-400 ng isolated phage DNA or 200 ng LD-PCR products, were cut individually with restriction enzymes ClaI, EcoRI, EcoRV, HindIII, PstI, SacI, SalI, XhoI and with enzyme combinations PstI/SalI and ClaI/SalI. The DNA fragments were separated in a 0.8% agarose gel, transferred to nylon membranes and hybridized with radioactively labeled cDNA clone 2-3-9 according to Sambrook et al., 1989. The evaluation of PCR and restriction analysis showed that 8 lambda clones contained genomic copy 1 of gene 2-3-9 and only one clone contains copy 2 of gene 2-3-9.

Figure 5:
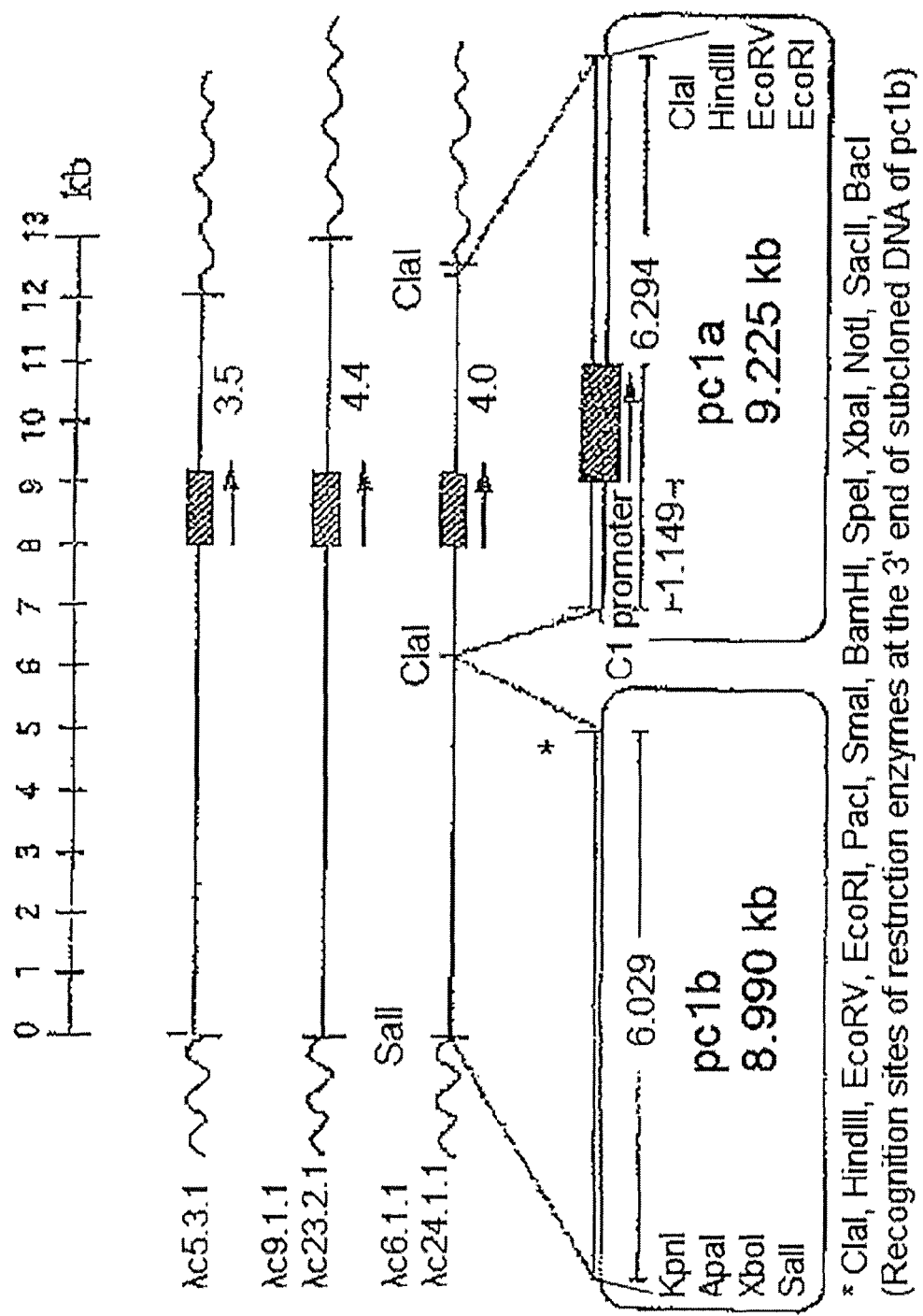
FIG. 5 shows the location and orientation of the coding region of the first copy of gene 2-3-9 and of the C1 promoter for 5 isolated lambda phages. Further, subcloning of the insert of phage λ 6.1.1 into plasmids pc1a and pc1b is depicted. Hatched box indicates the coding region for the first copy of gene 2-3-9.

Subcloning and Characterization of the C1 Promoter, which is Active in Above-Ground Organs Starting from 8 lambda clones, which carry genomic copy 1 of gene 2-3-9, the phage λ c6.1.1 was chosen for subcloning of the promoter. In the following, promoter of copy 1 of gene 2-3-9 is termed C1 promoter. The full-length coding region of the gene and the C1 promoter and the regulatory 3' region of the gene are located on a 6.294 kb ClaI-ClaI fragment. The ClaI-ClaI fragment was isolated from the DNA of phage λ c6.1.1 and subcloned into vector pBluescript II KS+ (Stratagene, Heidelberg, Germany), which was ClaI cleaved and dephosphorylated with alkaline phosphatase treatment. The resulting plasmid is termed pc1a. The nucleotide sequence of the subcloned fragment with the genomic fragment of copy 1 of gene 2-3-9 was determined. 1148 by of the determined nucleotide sequence are depicted as SEQ ID NO: 3. Nucleotides 1-1097 comprise the entire regulatory 5' region of the gene located on plasmid pc1a, and therefore comprise the C1 promoter. Comparison with the 5' end of the respective cDNA revealed that the transcribed, non-translated DNA sequence extends from position 984-1097. The position 1098-1148 are the first 51 translatable base pairs of the gene. The genomic 5' region following the C1 promoter was also subcloned from phage λ c6.1.1. For this, the phage DNA was cleaved with restriction enzymes SalI and ClaI, the isolated 6.026 kb SalI-ClaI fragment was subcloned into the corresponding restriction sites of vector pBluescript II KS+. The resulting plasmid is termed pc1b (FIG. 5).

Fusion of Sugar Beet C1 Promoter with the Luciferase Gene from *Photinus pyralis*

Figure 6:
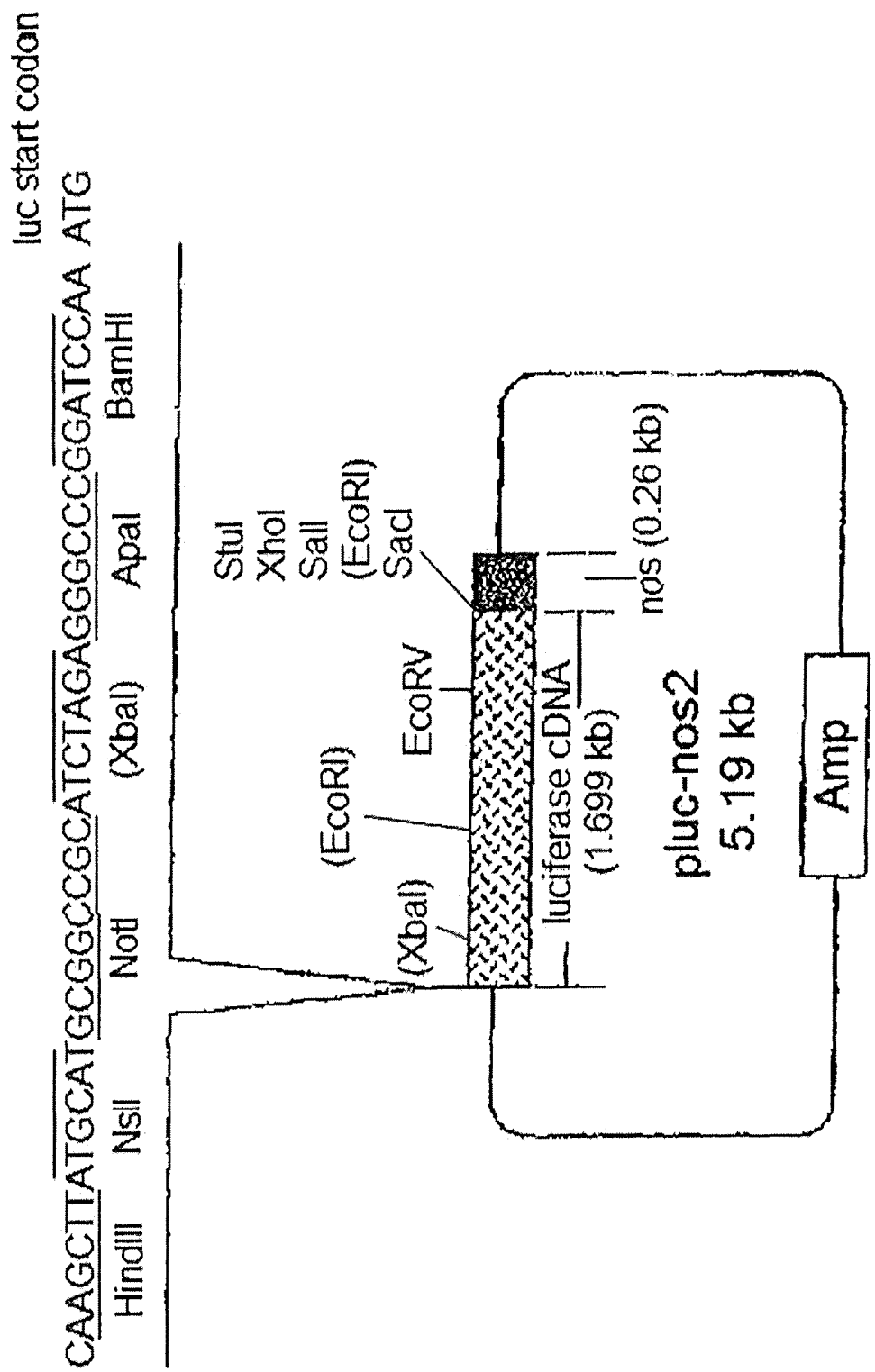
FIG. 6 shows the 5.19 kb reporter gene vector pluc-nos2. The plasmid pluc-nos2 comprises the luciferase gene from *Photinus pyralis* and the nos-terminator. The multiple cloning site in the 5'-region of the reporter gene allows the insertion of promoter fragments. The restriction enzymes in brackets cut the plasmid several times.
Figure 7:
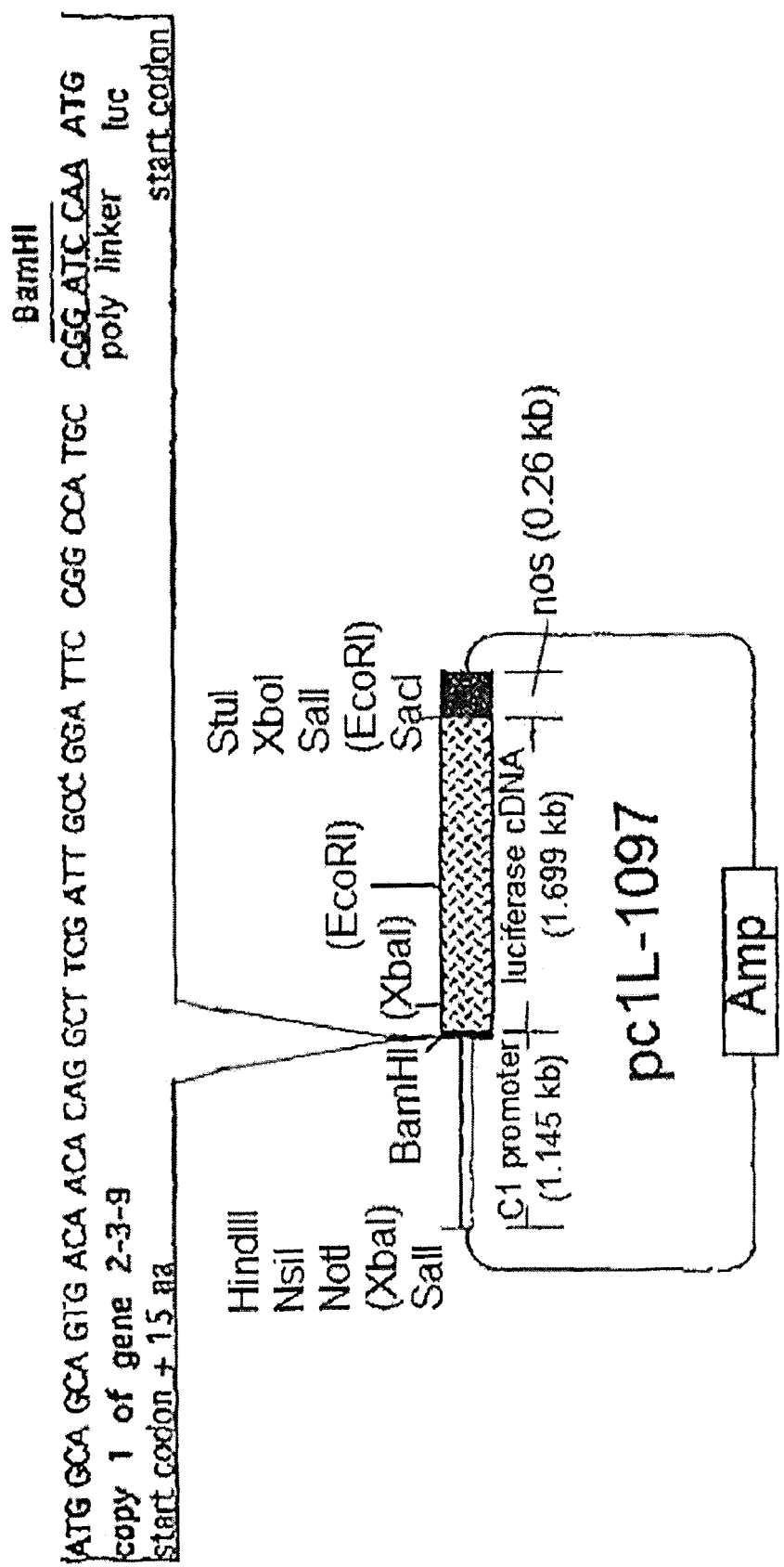
FIG. 7 shows the 6.34 kb reporter gene construct pc1L-1097. The vector pc1L-1097 is formed by insertion of the C1 promoter fragment (position 1-1145 of SEQ ID NO: 3) into vector pluc-nos2. The restriction enzymes in brackets cut the plasmid several times.
Figure 8:
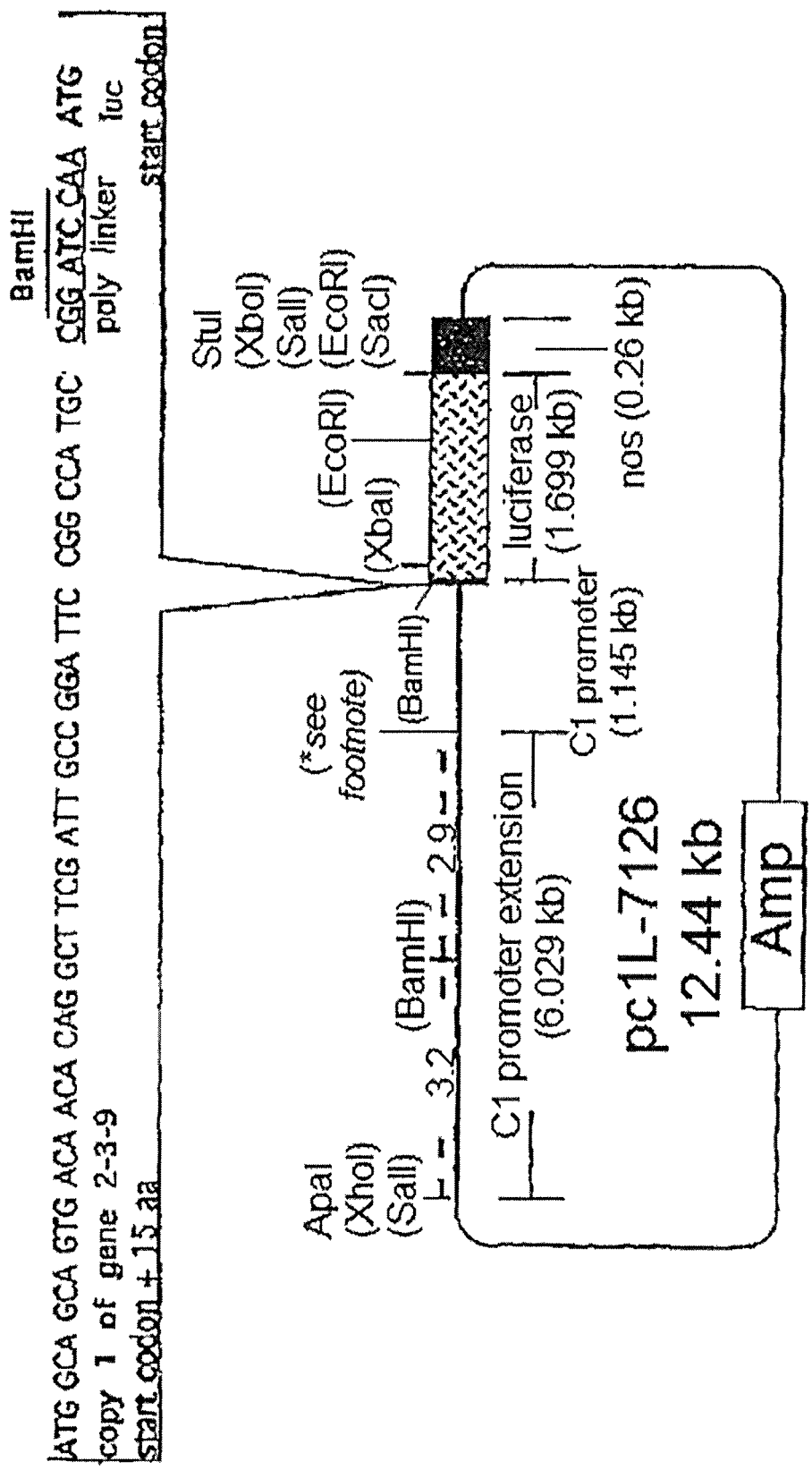
FIG. 8 shows the 12.44 kb reporter gene construct pc1L-7126. After isolation of the 6029 by genomic 5'-region of copy 1 of gene 2-3-9 from vector pc1b, the DNA fragment was inserted into vector pc1L-1097. The resulting vector pc1L-7126 comprises the regulatory 5'-region of the first copy of gene 2-3-9 from position 1-7126. The restriction enzymes in brackets cut the plasmid several times.

In order to determine the activity of the isolated C1 promoter in sugar beet leaves, the C1 promoter was translationally fused to the luciferase gene from *Photinus pyralis*. The reporter gene vector pGEM-luc (Promega, Mannheim, Germany), which carries the *P. pyralis* luciferase gene, was connected with the regulatory 3' region of the nopaline synthase (nos) gene, in order to obtain a vector suitable for expression in plants. For this, vector pBI101.3 (Clontech, Heidelberg, Germany) was linearized with EcoRI, and EcoRI DNA ends were modified by Klenow treatment to blunt DNA ends. By re-cleaving with SacI, the 0.26 kb nos terminator was set free, and then isolated. Vector pGEM-luc was linearized with restriction endonuclease SfiI, and the restriction site was blunted by T4 polymerase treatment. After restriction of the thus pre-treated vector with restriction enzyme SacI, the isolated 0.26 kb nos terminator was inserted as EcoRI (filled-in)-SacI fragment in pGEM-luc. The resulting vector is termed pluc-nos2 (FIG. 6). The C1 promoter fragment from position 1-1145 (SEQ ID NO: 3) was cleaved from the plasmid pc1a using the restriction enzymes SalI and AvrII, DNA ends were blunted by Klenow treatment and the promoter fragment was isolated. Vector pluc-nos2 was linearized with restriction enzyme ApaI, and the DNA ends were blunted by T4 polymerase treatment. After dephosphorylation of the vector, the C1 promoter was subcloned as SalI (filled-in)-AvrII fragment. The resulting vector is termed pc1L-1097 (FIG. 7). In vector pc1L-1097, the promoter is connected translationally with the luciferase gene by the base pairs of gene 2-3-9, coding for the first 16 amino acids. In order to answer the question, whether the C1 fragment used in pc1L-1097 is sufficient for promoter activity, this regulatory DNA fragment was enlarged by the adjacent genomic 5' region from sugar beet. For this, the 6029 by DNA fragment from pc1b was used. Plasmid pc1b was cleaved with restriction enzyme KpnI, and the DNA ends were blunted by T4 polymerase treatment. By recleavage with the restriction enzyme NotI, the genomic region could be isolated as KpnI (blunted)-NotI fragment, and could be cloned into vector pc1L-1097. The vector pc1L-1097 had first been linearized with HindIII, the DNA ends were blunted with Klenow fragment, and were then again treated with restriction enzyme NotI. The resulting plasmid is termed pc1L-7126 (FIG. 8) and comprises the 5' region of copy 1 of gene 2-3-9 from position 1-7126.

Detection of C1 Promoter Activity in Sugar Beet Leaves by Ballistic Transformation The activity of the reporter gene constructs pc1L-1097 and pc1L-7126 was measured in leaves after ballistic transformation. Ballistic transformation was carried out with a PDS-1000/He Particle Delivery Systems (BioRad) in accordance with the manufacturer's recommendations. As a microcarrier, gold powder type 200-03 (Heraeus, Hanau, Germany) with a particle size of 1.09-2.04 μm was used. Preparation and loading of the microcarrier with the reporter gene constructs was carried out according to BioRad protocol US/EG Bulletin 1688. The vectors pc1L-1097 and pc1L-7126 were used in equimolar amounts. In order to avoid result variations, which are based on different transformation efficiencies and not on differences of the strength of promoters, a normalization of the gene expression was conducted. For this, plasmid p70Sruc with the luciferase gene from Renilla reniformis as a second reporter gene system in a volume amount of 7:3 was mixed with vectors pc1L-1097 and pc1L-7126, respectively, and used for loading of the microcarrier. The measurement of a further reporter gene activity, which expression is under the control of the double 35S promoter, allows using this result as reference for the determination of the transformation efficiency of the single experiment.

For each of the reporter gene constructs to be tested, three shooting experiments were conducted, the gene expression was normalized, and then, a mean value of the normalized gene expression was calculated. For control purposes two shooting experiments were carried out with gold powder without DNA loading. Thus determined enzyme activities represent endogenous background activity in leaves, and were subtracted from further experimental values. Per shooting experiment, 13 leaf rondels were punched out with a cork drill (size 8) from young and old sugar beet leaves, and osmotically pretreated for 6 h in 90 mm petri dishes on MS medium+0.4 M mannitol solidified with agar at 25° C. Shooting parameters were 1550 psi burst disk size, 9 cm distance between leaf rondels and burst disk, and 27.5 in Hg negative pressure in the tool chamber. After shooting, the plates were incubated for 16 h at 25° C. under light.

Photinus and Renilla luciferace activity was determined with the dual luciferace reporter assay system (Promega, Mannheim, Germany) in a Lumat 9501 luminometer (PE Biosystem) according to the manufacturer's instructions. An enzyme extract suitable for measurement was obtained by maceration of the leaf rondels of one shooting experiment in liquid nitrogen. After vaporization of nitrogen, the powdery leaf material was homogenized with 10× volume (v/w) of passive lysis buffer (PLB). The liquid supernatant was transferred to a 1.5 ml Eppendorf tube and centrifuged for 5 min at 4° C. and 20,000 g. The clear supernatant was collected, and 10 μl raw extract was used for Photinus and Renilla luciferase activity measurement, respectively.

The mean value of the normalized gene expression for construct pc1L-1097 was 8.0 for small leaves and 9.6 for large leaves (table 4). For construct pc1L-7126, the mean value of the normalized gene expression was 3.2 for small leaves and 7.0 for large leaves (table 4). Therefore, the shorter C1 promoter fragment of plasmid pc1L-1097 in beet leaves is not only sufficient for the expression of the reporter gene, but it is also more active than the longer C1 promoter fragment of construct pc1L-7126.

Subcloning and Characterization of the C2 Promoter, Which is Active in Above-Ground Organs Subcloning of the promoter of the second copy of gene 2-3-9 resulted from phage λ c7.2.1. In the following, the promoter of this gene is indicated as C2 promoter. The preceding restriction analysis had shown that the 5' region of the coding region and approx. 3.0 kb of the regulatory 5' region of the second copy of gene 3-2-9 are located on a 4,002 kb PstI-PstI fragment of phage λ c7.2.1.

The 4,002 kb PstI-PstI fragment of phage λ c7.2.1 was isolated after PstI restriction digestion and cloned into vector pBluescript II KS+ (Strategene, Heidelberg, Germany). For this, vector pBluescript II KS+ was also cleaved with restriction enzyme PstI and then dephosphorylated by treatment with alkaline shrimps phosphatase (Roche Diagnostics GmbH, Mannheim, Germany). After ligation and transformation into E. coli strain XL-1, plasmid DNA was isolated from E. coli transformants, and positive clones were identified by restriction analysis. The resulting plasmid is termed pc2. The nucleotide sequence of the 4,002 kb PstI-PstI fragment was determined. 3049 by of the nucleotide sequence are depicted as SEQ ID NO: 4. Nucleotide 1-2998 comprise the entire regulatory 5' region of the gene located on plasmid pc2, and therewith the C2 promoter. The transcribed, non-translated DNA sequence, compared to the 5' end of the respective cDNA, extends from position 2928-2998. Position 2999-3049 are the first 51 translated base pairs of the gene.

Figure 9:
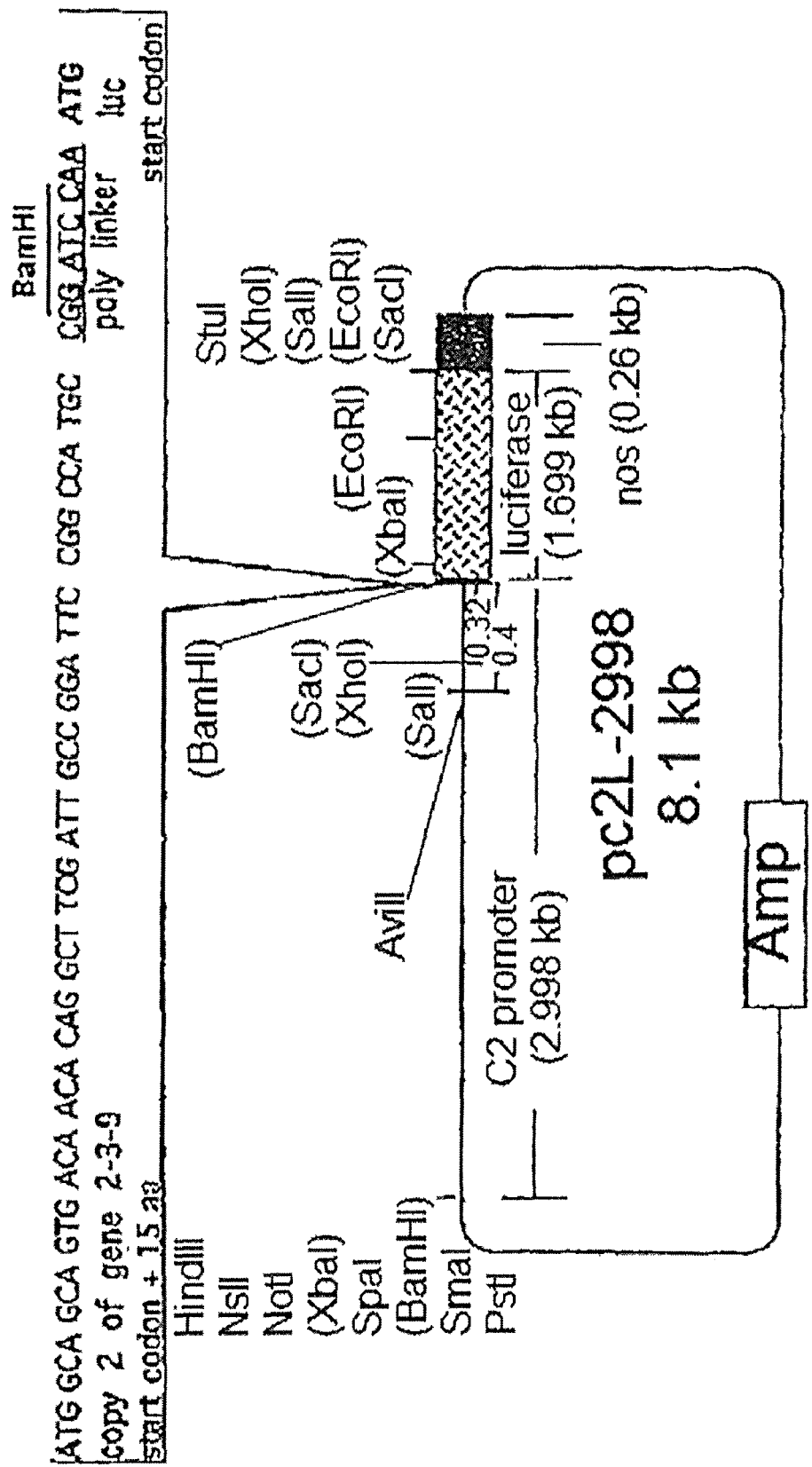
FIG. 9 shows the 8.1 kb reporter gene construct pc2L-2998. The vector pc2L-2998 is formed by insertion of the C2 promoter fragment (position 1-3046 of the nucleotide sequence of SEQ ID NO: 4) into vector pluc-nos2. The restriction enzymes in brackets cut the plasmid several times.

Fusion of Sugar Beet C2 Promoter with the Luciferase Gene from Photinus pyralis and Preparation of Deletion Constructs In order to detect the activity of the isolated C2 promoter in sugar beet leaves, the C2 promoter was translationally fused to the luciferase gene from Photinus pyralis. For this, the 4002 by DNA fragment subcloned in pc2, comprising the C2 promoter and the 5' region of the coding region of the second copy of gene 2-3-9 was isolated after restriction digestion with enzymes NotI and EcoRI. The DNA fragment was then partially cleaved with enzyme AviII, and an approx. 3100 by NotI-AviII fragment was isolated, which comprises base pairs 1-3046 of SEQ ID NO: 4. The NotI-AviII fragment was then subcloned into reporter gene vector pluc-nos2. For this, vector pluc-nos2 was first cleaved with restriction enzyme ApaI, and the sticky ends were blunted by T4 polymerase treatment. By recutting with restriction enzyme NotI, vector pluc-nos2 was transferred into a condition susceptible for receiving the NotI-AviII fragment. The resulting fragment is termed pc2L-2998 (FIG. 9). Vector pc2L-2998 carries the C2 promoters sequence of SEQ ID NO: 4 from nucleotide position 1-2998 and the first 48 translated base pairs of gene 2-3-9 from position 2999-3046.

Figure 10:
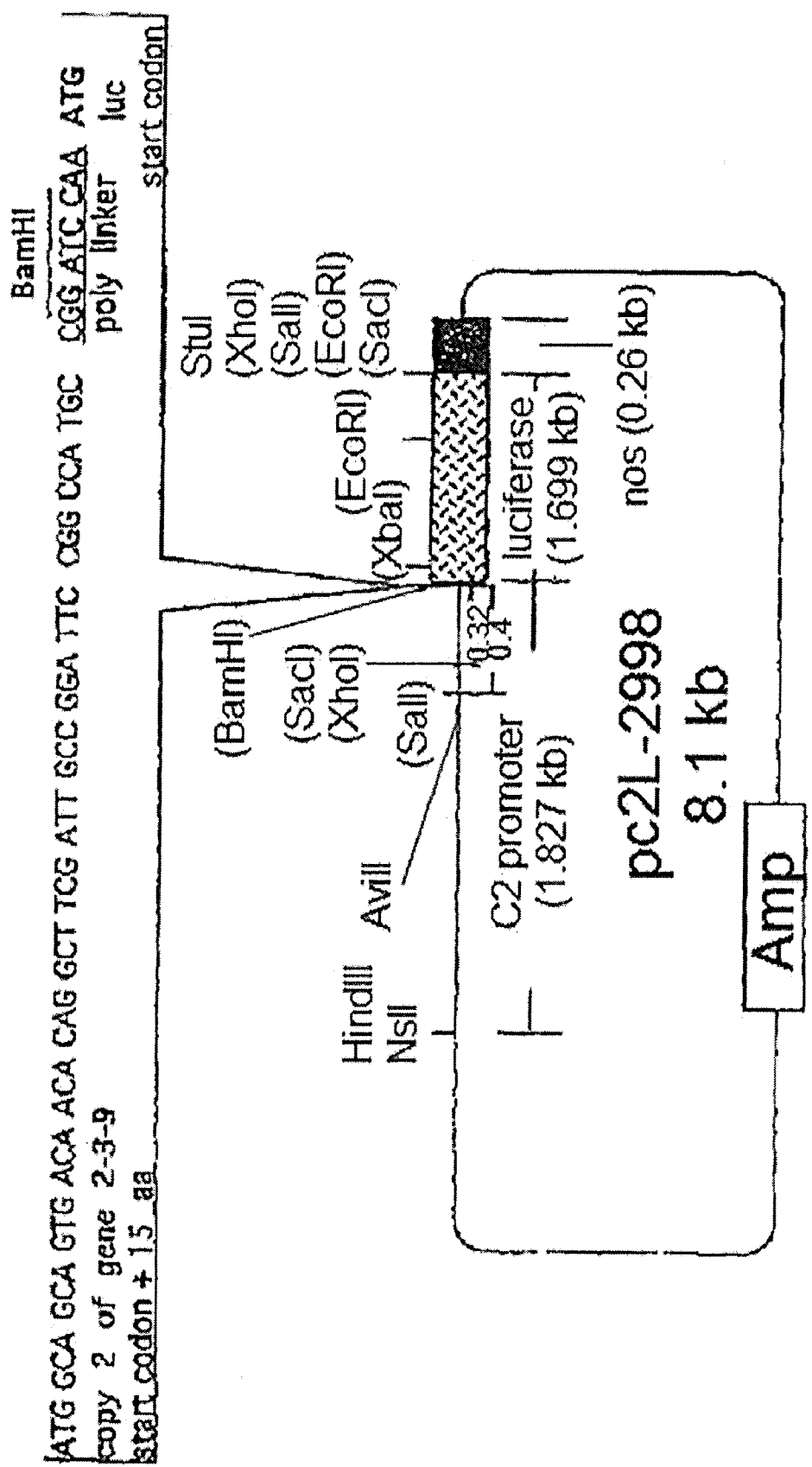
FIG. 10 shows the 6.9 kb reporter gene construct pc2L-1827. The vector pc2L-1827 is formed by a 5'-deletion of the C2 promoter of plasmid pc2L-2998. The C2 promoter in vector pc2L-1827 comprises the nucleotide positions 1172-

In order to identify the minimal DNA fragment size, which is necessary for the activity of the C2 promoter, three 5' deletion constructs were prepared. Constructs pc2L-1827, pc2L-989 and pc2L-342 comprise the C2 promoter sequence of SEQ ID NO: 4 from nucleotide position 1172-2998, 2011-2998 and 2657-2998, respectively, and the first 48 translated base pairs of gene 2-3-9 from position 2999-3046 (FIG. 10-12). Based on pc2L-2998, the vectors were developed in detail as follows:

Vector pc2L-1827 by a restriction digestion with enzymes KpnI and NotI, a subsequent blunting of the DNA ends with T4 polymerase treatment and religation of the vector.

Plasmid pc2L-989 by a digestion with restriction enzyme SmaI and religation of the vector.

Plasmid pc2L-342 by a digestion with restriction enzyme NotI and a partial SalI digest. After blunting of the DNA ends by Klenow treatment, the vector was religated.

Detection of C2 Promoter Activity in Sugar Beet Leaves by Ballistic Transformation The activity of reporter gene constructs pc2L-2998, pc2L-1827, pc2L-989 and pc2L-342 was determined in leaves after ballistic transformation. Ballistic transformation and determination of reporter gene activities were done as previously described for the C1 promoter. Vectors pc2L-2998, pc2L-1827, pc2L-989 and pc2L-342 were used in an equimolar ratio. In order to avoid result variations, which are based on different transformation efficiencies and not on differences in promoter activities, a normalization of the gene expression was done with the help of plasmid p70Sruc. Plasmid P70Sruc carries the luciferase gene from *Renilla reniformis* as a second reporter gene system. For each reporter gene construct to be investigated, four shooting experiments per DNA preparation were conducted. For constructs pc2L-2998 and pc2L-1827 one DNA preparation was used and for constructs pc2L-989 and pc2L-342 two DNA preparations were used. The measured gene expression was normalized and then, a mean value of the normalized gene expression was calculated. For control purposes four shooting experiments with gold powder without DNA loading were conducted. The mean value of the normalized gene expression for constructs pc2L-2998, pc2L-1827, pc2L-989 and pc2L-342 was in detail 8.0, 4.5, 6.45 and 6.45, respectively (FIG. 13). Therefore, all C2 promoters fragments are suitable to allow the expression of a gene in leaves. The smallest promoter fragment of construct pc2L-342, which refers to nucleotide sequence of SEQ ID NO: 4 from position 2657-3046, is equally active as the larger promoter fragments of constructs pc2L-2998, pc2L-1827 and pc2L-989.

Construction of Plant Transformation Vectors pc1G-1097 and pc2G-2998 as an Example For the stable transformation of gene fusions of C1 and C2 promoters, active in above-ground organs, and the gus reporter gene, binary vectors pc1G-1097 (FIG. 14) and pc2G-2998 (FIG. 15), were developed.

For construction of pc1G-1097, the C1 promoter is isolated from vector pc1L-1097 as approx. 1.17 kb HindIII-BamHI fragment and inserted into the HindIII and BamHI linearized binary vector pBI101.3 (Clontech, Heidelberg). Subcloned C1 promoter comprises the nucleotide sequence of SEQ ID NO: 3 from position 1-1145. In the resulting vector pc1G-1097, the C1 promoter is linked translationally with the gus gene from pBI101.3 by the base pairs coding for the first 16 amino acids of gene 2-3-9.

Vector pc2G-2998 is constructed in such a way that the C2 promoter is isolated from vector pc2L-2998 and translationally linked to the gus gene from pBI101.3. Vector pc2G-2998 carries, like plasmid pc2L-2998, the C2 promoter sequence of SEQ ID NO: 4 from nucleotide position 1-2998 and the first 48 translated base pairs of gene 2-3-9 from position 2999-3046. For this, pc2L-2998 was cleaved with restriction enzyme PstI, and the DNA ends were blunted by Klenow treatment. After treatment with restriction enzyme BamHI, the C2 promoter could be isolated as approx. 3070 by DNA fragment and cloned into adequately prepared binary vector pBI101.3. For insertion of the C2 promoter, vector pBI101.3 was initially linearized with restriction enzyme SalI, and the DNA ends were filled-in by Klenow treatment. The vector was then cleaved with enzyme BamHI.

Transformation of Constructs pc1G-1097 and pc2G-2998 in Plants

The constructs defined for the production of transgenetic plants are initially transferred into *Agrobacterium tumefaciens* strain GV2260 by a direct DNA transformation method (An, 1987). The selection of recombinant *A. tumefaciens* clones is carried out by using the antibiotic kanamycin (50 mg/l). In the following, as an example, the transformation for vector pc1G-1097 is described.

The reporter gene cassette consisting of the translational fusion between the C1 promoter and the gus gene is transformed into summer *brassica* genotype Drakkar with the help of *A. tumefaciens* according to Horsch et al., (1985). Transgenetic plants are selected with the antibiotic kanamycin. The presence of the promoter in transgenetic plants can be verified by PCR. The use of primers GTGGAGAGGCTATTCGGTA (SEQ ID NO: 9) and CCACCATGATATTCGGCAAG (SEQ ID NO: 10) leads to the amplification of a 535 by DNA fragment from the nptII gene. PCR is done with 10 ng genomic DNA, a primer concentration of 0.2 µM at an annealing temperature of 55° C. in a multicycler PTC-200 (MJ Research, Watertown, USA).

Using the above described techniques, twenty independent *brassica* and tobacco transformants were obtained with binary vector pc1G-1097, respectively, and twenty independent *brassica* and potato transformants were obtained with binary vector pc2G-2998, respectively.

Determination of C1 and C2 Promoter Activity in Leaves of Transgenetic *brassica*, Potato and Tobacco Plants In order to determine the activity of C1 and C2 promoters in leaves of transgenetic *brassica* and tobacco plants, a histochemic GUS staining was done. Leaves are taken from transgenetic and non-transgenetic in vitro plants, vacuum infiltrated with GUS staining solution (2 mM 5-bromo-4-chloro-3-indoyl-beta-glucuronide, 50 mM sodium phosphate pH 7.0, 0.5% Triton X-100, 2% N,N-dimethylformamide) for 15 sec, and then incubated for 16 h at 37° C. Then, chlorophyll from leaves is extracted with 70% ethanol. Blue staining of the tissue indicates regions in which GUS activity is present and the promoter is expressed.

Leaf portions from *brassica* transformant pc1G-1097-86 and tobacco transformant pc1G-1097-3 show an intensive even blue staining of the tissue (FIGS. 16 and 17). In comparison thereto, leaf portions of non-transgenetic *brassica* and tobacco plants are white after this treatment. Also intensively blue stained are leaf portions of potato transformant pc2G-2993-1. These results show that C1 and C2 promoters in stable transformed *brassica*, potato and tobacco plants are functional, and that the gus reporter gene under the control of the promoter is expressed in the family of Brassicaceae and Solanaceae.

Homology Between C1 and C2 Promoters

Nucleotide sequence comparison between DNA sequences of promoters C1 and C2 shows that the promoter region of the C1 promoter from position 780-1051 with the exception of three base pairs is entirely identical with the sequence of the C2 promoter from position 2707-2984 (FIG. 18). The sequences of the C1 promoter from position 1-799 do not show any significant homology to the DNA sequence of the C2 promoter from position 1-2706. The homologue region between the promoters comprises positions from −320 to −42 of the C1 promoter and the positions from −292 to −21 of the C2 promoter with respect to the translation start. In the homologue promoter region next to the TATA box and the respective transcription start are multiple cis-elements, which are conserved between both promoters. In C1 promoter, the TATA box extends from position 950-956 and in C2 promoter from position 2877-2883. Next to the TATA box, among the elements, which are frequently found in promoters, are a CAAT box at position 884-887 in C1 promoter and at position 2811-2814 in C2 promoter. Among the cis-elements specific for C1 and C2 promoters are a 4.times. repeat of the GATA box at positions 812-815, 820-823, 832-835 and 838-841 in the C1 promoter and at the positions 2739-2742, 2747-2750, 2759-2762 and 2765-2768 in the C2 promoter. The GATA box was identified in the 35S promoter as binding site for the ASF-2 transcription factor and is present in a 3.times. repeat in the light regulated promoter of the chlorophyll a/b binding protein of petunia (Lam and Chua, 1989). At position 832-837 of the C1 promoter and at position 2759-2764 of the C2 promoter is an I box with the sequence GATAAG. The I box was first described for the light regulated rbcS promoters of tomato and arabidopsis (Giuliano et al., 1988). At positions 844-849 and 985-990 of the C1 promoter and positions 2771-2776 and 2912-2917 of the C2 promoter a 2.times. repeat of the GT-1 binding site is located. The GT-1 binding site with the consensus sequence G(A/G)(A/T)AA(A/T) was described for promoters of several light induced genes and the pathogen resistance gene PR-1 (Zhou, 1999). A 2.times. repeat of a DNA sequence, which is important for circadian expression is located at positions 913-922 and 1014-1023 in the C1 promoter and at the positions 2840-2849 and 2941-2950 in the C2 promoter. The circadian box with the consensus sequence CAANNNNATC (SEQ ID NO: 11) was identified in a light regulated Lhc promoter of tomato (Piechulla et al., 1998).

Change of the Carbohydrate Metabolism of Plants by Use of Root Specific Promoters 2-1-48 and 2-1-36, Exemplified by Avoidance of Storage Substance Loss The carbohydrate metabolism of plants can specifically be improved by the use of root specific promoters of genes 2-1-48 and 2-1-36. As an example, the expression of the invertase inhibitor gene from tobacco (Greiner et al., 1998) in the root of sugar beets under control of root specific active promoters 2-1-48 and 2-1-36, respectively, is described. By root specific expression of the storage substance losses, which are present after the root harvest until root processing, sucrose and sugar, technically undesired accumulation of glucose and fructose, is reduced, and thereby the sugar yield is altogether improved. Using a root specific promoter allows, in contrast to a promoter, which is constitutively active in all tissues, to restrict the expression of the invertase inhibitor gene to the root. By this regional restriction, undesired yield-reducing effects, which would be present if the inhibitory gene were expressed in all plant parts, are avoided.

Promoters 2-1-48 and 2-1-36 can be connected to the tobacco invertase inhibitor gene, respectively, as translational or transcriptional fusion and transferred by A. tumefaciens mediated transformation into sugar beet. For this purpose the respective binary vectors are trans-formed into A. tumefaciens isolate C58 ATHV according to An (1987). The plant starting material for transformations of sugar beets are seedlings. For this, seeds of the sugar beet are surface disinfected with 12% sodium hypochloride, and then germinated for 3-4 weeks under sterile conditions. The seed leaves of these seedlings are then cut with the help of a scalpel and incubated for 5-10 min in a diluted overnight culture of A. tumefaciens isolates (OD 0.2-0.3). Then plant parts are swap-dried and cocultured for 3 days on solid 1/10 MS medium+30 g/l sucrose. After the cocultivation phase, the explants are transferred to selection medium (MS medium+0.25 mg/l BAP, 0.05 mg/l NAA), 500 mg/l betabactyl, 20 g/l sucrose). For selection of transformants kanamycin is used. After 7-12 weeks, transgenetic plants develop, which can be propagated and rooted.

In order to detect the transgenetic character of the plants molecular biologically, the nptII gene transferred to the plants is detected as described by two gene specific primers. Expression of the invertase inhibitor gene in sugar beet roots is detected by RNA blot studies. For this, clone plants starting from primary transformants and non-transgenetic control plants are produced and transferred into a greenhouse for further culturing. RNA is isolated from leaves, petioles and the root of invertase inhibitor and control plants according to Logemann et al. 1987, as previously described, gel-electrophoretically separated and transferred to a nylon membrane. The subsequent hybridization with the invertase inhibitor gene from tobacco shows that the gene is only expressed in the root and not in above-ground organs of the transgenetic plants. In order to analyze the positive effect to the root specific expression, a storage experiment is conducted.

The fully developed storage roots from 24 week old inhibitor and control plants are harvested and superficially injured by a 30 seconds treatment in a commercially available cement mixer (Attika) in order to create injuries typical for mechanical beet harvest. Subsequently the beets are stored at 17° C. and 27° C. From plant material stored at 17° C. 1, 3, 4, 7, 14, 21, 28, 35 and 46 days after harvest and from the beets stored at 27° C. 1, 3, 4, 7 and 14 days after harvest 5 beets are withdrawn, respectively. The beets are homogenized and the content of fructose, glucose and sucrose is determined. Non-transgenetic sugar beets stored at 17° C. and 27° C. show, beginning at the fourth storage day, a significant increase of glucose and fructose content and a decrease of sucrose concentration. In contrast, the storage roots of the invertase inhibitor plants comprise less accumulation of glucose and fructose and less decrease of sucrose concentration in comparison to the control plants.

Change of the Carbohydrate Metabolism of Transgenetic Roots by Use of the Root Specific Promoters 2-1-48 and 2-1-36 Exemplified by the Reduction of Wound Induced Vacuolar Invertase Activity The described improvement of the carbohydrate metabolism of plants can also be detected by transgenetic root cultures ("hairy root") of the sugar beet. Three A. tumefaciens C58 ATHV derivatives, which are transformed with the 2-1-48 promoter inhibitor construct, the 2-1-36 promoter inhibitor construct or only with the parent vector, respectively, are grown for 24 h in liquid LB medium+50 mg/l kanamycin. In parallel, Agrobacterium rhizogenes strain 15834 is cultured in liquid TSB medium+25 mg/l rifampicin. Subsequently, A. tumefaciens and A. rhizogenes strain are cultured for 21 h in the respective medium without antibiotics. Optical density of the bacterial cultures is determined and adjusted to $A_{600}$=0.4-0.6. Leaf stalks of 3-4 week old sugar beets, which were cultured under in vitro conditions, are cut into 0.5 cm portions and shortly dipped in a 1:1 mixture of the A. tumefaciens and A. rhizogenes cultures. The leaf portions are cocultered with the bacteria for 2 days under constant light and 25° C. on solid MS medium+0.5 mg/l BAP. After cocultivation, the stem segments are transferred to solid MS medium+0.5 mg/l BAP+ 350 mg/l betabactyl (SmithKlineBeecham)+150-300 mg/l kanamycin, and incubated under weak light. After approx. 12 days, the first transgenetic roots are visible, which are cut-off and propagated on ½ B5 medium+300 mg/l betabactyl+300 mg/l kanamycin. The transgenetic root cultures are propagated for further experiments on ½ B5 medium without antibiotics.

The expression of the invertase inhibitor gene from tobacco in transgenetic root cultures is detected by an RNA blot experiment. RNA is isolated from root cultures, which were transformed with the 2-1-48 promoter inhibitor construct, the 2-1-36 promoter inhibitor construct and the parent vector, respectively. The RNA is gel-electrophoretically separated, blotted, and the nylon filter is hybridized with a radioactively labeled invertase inhibitor gene as probe. The hybridization result shows that the invertase inhibitor gene of tobacco is only expressed in root cultures transformed by the 2-1-48 promoter inhibitor construct and the 2-1-36 promoter inhibitor construct, but not in root cultures transformed by the parent vector for control purposes.

The improvement of the carbohydrate metabolism of root cultures is proven by the determination of wound induced vacuolar invertase activity. The acid vacuolar invertase of the sugar beet is localized in the vacuole, like sucrose. During the first 12 days after beet harvest an increase of the inverted sugar concentration and of activity of the acid vacuolar invertase is observed. The wounding of the beet body by decapitation of the sugar beet and the subsequent harvest procedure and the interruption of the vegetation period are regarded as the reasons for the induction of the acid invertase activities and therewith the increase of inverted sugar in the beet (Berghall et al., 1997).

By root specific expression of tobacco invertase inhibitor gene in transgenetic root cultures, the activity of vacuolar invertase in reaction to the wound stimulus is strongly induced and the formation of inverted sugar is dramatically reduced. Root cultures, which were transformed with the 2-1-48 promoter inhibitor construct, the 2-1-36 promoter inhibitor construct and the parent vector, respectively, are cut with a scalpel into 3 mm portions and are incubated for 24 and 48 h in liquid ½ B5 medium. Subsequently, the roots are homogenized and the activity of acid vacuolar invertase is determined. Cultures, in which the inhibitor is root specifically expressed by promoters 2-1-48 and 2-1-36 show in reaction of the wounding significantly less activity of acid vacuolar invertase and therewith an improved carbohydrate metabolism in comparison to control probes.

Change of the Carbohydrate Metabolism of Plants by Using the Root Specific Promoters 2-1-48 and 2-1-36 Exemplified by the Synthesis of New Carbohydrates The carbohydrate metabolism of plants can be significantly improved by the use of root specific promoters of genes 2-1-48 and 2-1-36 in order to produce new carbohydrates. As an example, the synthesis of the sugar substitute palatinose and the sweetener palatinite in roots of sugar beets under the control of root specifically active promoters 2-1-48 and 2-1-36 is described.

Palatinite (glucosyl-α-(1,6)-sorbit/mannit) can be synthesized starting from sucrose in two reaction steps. Sacchrose-6-glucosylmutase catalyses the conversion of sucrose into palatinose (isomaltulose). Palatinose is reduced by sorbit dehydrogenase into palatinite (isomalt).

The combination of root specific promoters 2-1-48 and 2-1-36 with a fusion between the vacuolar transit peptide of potato palatine gene and the gene for saccharose-6-glucosylmutase from *Pseudomonas mesoacidophila* or *Protaminobacter rubrum* (Klein, 1995), respectively, allows the production of transgenetic plants, which produce palatinose specifically in roots only. These constructs are transformed, as previously described, in plants like sugar beet, which incorporate the storage substance sucrose in root vacuoles. As a selection marker the nptII gene in combination with the antibiotic kanamycin is used. The transgenetic character of sugar beets identified by kanamycin selection, is verified by PCR, using primers specific for the nptII gene.

The concentration of palatinose in roots of different transformants is determined by HPLC. The probes can be separated by application of the running agent 0.1 M NaOH on a Hamilton RCX-10 (250×4.1 mm) column. The quantification of palatinose in root extracts is done by referring to palatinose references of known concentration. Using this analytical technique, sugar beet transformants can be identified, which produce palatinose in roots.

For the preparation of palatinite producing plants, palatinose sugar beets are selected, which accumulate the highest concentration of palatinose in the root. These transformants are transformed once again with a construction, which comprises the 2-1-48 and 2-1-46 promoter in combination with the sorbit dehydrogenase gene, respectively. Therefore, the dehydrogenase gene is on the one hand fused to a vacuolar transit sequence or free of a signal sequence, so that the gene product is localized in the cytoplasm. For the selection of double-transformants a binary vector is used, which either comprises the pat or the CP4 gene so that basta or roundup can be used as selection agent. Transformants, which comprise such a herbicide resistance are additionally molecular biologically characterized by PCR by determining the presence of the bar and the CP4 gene, respectively.

The synthesis of palatinite in transgenetic plants is quantitatively determined by HPLC. These investigations show that the coexpression of a bacterial saccharose-6-glucosylmutase gene in combination with a sorbit dehydrogenase gene, using root specific promoters, leads to the formation of palatinite. Only the use of root specific promoters allows, in comparison to constitutive promoters, to obtain transformants, which show a normal phenotype and produce palatinite without undesired physiological amendments in commercially interesting concentrations.

Variation of the Carbohydrate Metabolism of Transgenetic Roots by Using Root Specific Promoters 2-1-48 and 2-1-36, Exemplified with the Synthesis of New Carbohydrates An improvement of the carbohydrate metabolism of plants by synthesis of new carbohydrates can also be demonstrated by transgenetic root cultures ("hairy root") of sugar beet. For this purpose, the previously described expression cassettes consisting of the 2-1-48 and 2-1-36 promoter and the fusion between the transit sequence of the palatine gene with the gene for saccharose-6-glucosylmutase from *Pseudomonas mesoacidophila* and *Protaminbacter rubrum* and the 2-1-48 and 2-1-36 promoter and the sorbit dehydrogenase gene, respectively, are integrated into the binary vector BIN19 (Clontech, Heidelberg, Germany). The resulting constructs are transformed into *A. tumefaciens* strain C58 ATHV. By cotransformation with *A. rhizogenes* strain 15834, the gene combination of saccharose-6-glucosylmutase and sorbit dehydrogenase is transformed, as described, in transgenetic sugar beet roots.

The quantitative detection of palatinite is done by HPLC, as described. These analytical analyses show that the expression of the saccharose-6-glucosylmutase and sorbit dehydrogenase gene under the control of root specific promoters 2-1-48 and 2-1-36 leads to the formation of the new carbohydrate palatinite in transgenetic root cultures.

Variation of the Carbohydrate Metabolism of Plants by Using Root Specific Promoters 2-1-48 and 2-1-36, Exemplified by the Synthesis of Novel Polymers The carbohydrate metabolism of plants can be specifically improved by using root specific promoters of genes 2-1-48 and 2-1-36 by the production of new polymers.

The formation of new polymers can, for example, occur in roots of sugar beets by expression of a fructan-fructan-fructosyl transferase, a sucrose-sucrose-fructosyl transferase, a levan sucrase, a sucrose-fructan-6-fructosyl transferase and a fructosyl transferase.

The coding regions of the enzymes are each connected with the root specific promoter of genes 2-1-48 and 2-1-36 and transformed into sugar beets with the help of *A. tumefaciens* according to techniques known in the art, and transferred by cotransformation with *A. rhizogenes* in transgenetic root cultures, respectively. The expression of transferred genes is determined on the one hand by RNA blot studies using coding regions as hybridization probes and on the other hand by enzymatic activity measurement. By sugar analytical measurements, transformants can be identified, which comprise the desired polymers in highest concentration.

Variation of the Nitrogen Metabolism of Plants by Using Root Specific Promoters 2-1-48 and 2-1-36 and C1 and C2 Promoters, Respectively, Active in Above-Ground Organs The nitrogen metabolism of plants can be improved in various aspects by using root specific promoters of genes 2-1-48 and 2-1-36 and by using C1 and C2 promoters, which are active in above-ground organs. The root and leaf specific increase of the number of suitable transport proteins improves the uptake and the transport of N-compounds in the plant.

By using root specific expression of transporter protein genes for ammonium ($NH_4^+$), nitrate ($NO_3^-$) and nitrite ($NO_2^-$) ions, the nitrogen uptake from the ground can be increased and the use of N-fertilizer can be improved. The leaf specific expression of nitrate and nitrite transport proteins serves for an efficient use of N-compounds already taken up into the root by using promoters C1 and C2, which are active in above-ground organs. The leaf specific expression of nitrate transport proteins leads to an increased phloem discharge of nitrate ions and to an increased nitrate uptake into leaf parenchyma cells. The N-reduction in plastids is increased by elevated nitrate accumulation in leaf parenchyma cells. The elevated transport of nitrite from the cytosol into the plastids by leaf specific expressions of suitable nitrite transport protein also leads to an increase amino acid biosynthesis.

Increase of Tolerance Towards Pathogens by Using Root Specific Promoters 2-1-48 and 2-1-36 and/or of Promoters C1 and C2, which are Active in Above-Ground Organs Root specific promoters 2-1-48 and 2-1-36 and promoters C1 and C2, which are active in above-ground organs can be used for the development of features, which improve the resistance or tolerance towards pathogens.

Increase of Tolerance Towards Phytopathogenic Viruses by Use of Root Specific Promoters 2-1-48 and 2-1-36 and/or Promoters C1 and C2, which are Active in Above-Ground Organs Numerous phytopathogenic viruses of the sugar beet show organ specificity, i.e. the viral multiplication does usually not occur in the entire plant, but only in one specific organ or tissue type. Also, damages, which are induced by the viral infection are generally restricted to the infected organ. Viral pathogens of the sugar beet with organ specificity are, e.g. BNYVV with a preference for root and BMYV and BYV with a restriction to beet leaves.

Root specific promoters 2-1-48 and 2-1-36 can be used in order to develop a root specific BNYVV resistance in sugar beet. For this, for the realization of gene silencing dependent virus resistance strategy, a native or mutagnized DNA partial sequence of the viral BNYVV genome is combined with the 2-1-48 or 2-1-36 promoter. The combination between the promoter sequence and the viral DNA sequence is designed such that the transcription of the BNYVV sequence leads to a gene silencing, effective against BNYVV. The efficiency of this approach is determined by the determination of the virus titer in plants by using an ELISA test, which is directed against the core protein of BNYVV.

Increase of Tolerance Towards Phytopathogenic Nematodes by Using Root Specific Promoters 2-1-48 and 2-1-36

The root specific activity of promoters 2-1-48 and 2-1-36 can be used to induce in plants as sugar beet a resistance towards nematodes like *Heterodera schachtii* or in potatoes a resistance towards *Globodera pallida* or *Globodera rostochiensis*.

For this purpose, a nematode resistance gene or a gene for a nematocid acting compound is translationally or transcriptionally fused with promoter 2-1-48 and 2-1-36, respectively, and inserted in a binary plant transformation vector like, e.g. BIN19. Nematode resistance genes, which mediate a resistance towards *Heterodera schachtii*, are $Hs1^{pro-1}$ from *Beta procumbens* (Cai et al., 1997) and in the case of *Globodera pallida* the Gpa2 gene of potato (Van der Vossen et al., 2000).

By *A. tumefaciens* mediated transformation, the promoter gene combinations are used in an already described manner for the yield of transgenetic sugar beets or potatoes. Further, the gene constructs can be transferred into transgenetic root cultures of the sugar beet by cotransformation using *A. tumefaciens* and *A. rhizogenes* according to the described protocol. The transgenicity of produced plants is molecular biologically detected by PCR by amplification of the nptII gene. The root specific expression of the resistance mediating factor, as, e.g. $Hs1^{pro-1}$ gene, is proven by an RNA blot study using the $Hs1^{pro-1}$ gene as hybridization probe. The resistance of the transgenetic plants and transgenetic root cultures is examined and determined by a nematode resistance test. The realization of nematode resistance testing with *H. schachtii* on transgenetic root cultures of sugar beet is described by Cai et al., (1997). The person skilled in the art will find the experimental description of the resistance test of in vitro potatoes towards *G. pallida* or a reference to the realization of greenhouse testings in (Van der Vossen et al., 2000).

The advantages of root specific expression of the nematode resistance gene and the nematocid component are the high resistance and the fact that the resistance mediating gene products are only produced in the organ to be protected. The absence of the resistance mediating gene product in plant parts, which are intended for consumption, like the potato bulb, increases the social acceptance and thereby the chances for sales of the transgenetic plant and the product derived thereof.

Increase of Tolerance of Transgenetic Plants Towards Pytophatogenic Fungi by Use of Root Specific Promoters 2-1-48 and 2-1-36 and/or Promoters C1 and C2, which are Active in Above-Ground Organs Root specific promoters 2-1-48 and 2-1-36 and promoters C1 and C2, which are active in above-ground organs, can be used to develop a direct or indirect antifungal effect in plants in combination with a gene or gene combination. The antifungal effect leads to the feature of increased fungus resistance or fungus tolerance.

The root specific promoters 2-1-48 and 2-1-36 and the promoters C1 and C2, which are active in above-ground organs, are translationally or transcriptionally fused with genes of pathogen defense, respectively, which gene products have a direct antifungal activity. The promoter gene combinations are cloned into the binary transformation vector BIN19 and transformed into sugar beet, potato and *brassica* by *A. tumefaciens* mediated transformation. The transgenicity of the plants is tested by PCR, as described, and the expression of the gene in roots or leaves is verified by RNA blot studies. Increased fungus resistance of plants is observed in fungus resistance assays, as they are exemplarily described in the following for resistance testing of sugar beets towards *Cercospora beticola.*

For infection of sugar beets with the leaf spot pathogen *C. beticola*, sugar beets of the tolerant genotype 1K0088 and of the susceptible genotype 3S0057 are cultured in addition to transgentic plants under greenhouse conditions. Two weeks before the intended inoculation 20 V8 vegetable juice plates (40% Albani vegetable juice) are inocluated with four different *C. beticola* isolates and incubated at 25° C. Immediately before inoculation, the fungus grown agar is homogenized with 0.5 1 water in a high performance agitator (UM5 Universal, Stephan). The concentration of mycelium fragments and fungus spores in the homogenate is determined with the help of a counting chamber. The inoculum density is adjusted to a concentration of 100,000 fragments/ml by dilution with water. The diluted homogenate is spread onto 12 week old sugar beet with the help of a backpack sprayer (Gloria 176T). For control purposes, plants are sprayed with fungus-free agar homogenate. The plants are incubated after inoculation for 4 days at 25° C. and 95% humidity in a greenhouse. After day four, humidity is reduced to 60-70%. Fourteen and twenty-one days after inoculation, the infection of the leaves by fungus and agar inoculated plants are optically determined.

Transgenetic sugar beets show, e.g. in case of the use of promoters, which are active in above-ground organs, an increased resistance towards the leaf parasites *Cercospora beticola* and also an increased resistance towards *Ramularia beticola* and *Erysiphe betae*. Sugar beets, in which the pathogen defense genes are root specifically expressed, comprise an increased resistance towards the parasites *Rhizoctonia solani* and *Aphanomyces cochlioides.*

Surprisingly, the organ specific constitutive expression of pathogen defense genes does not lead to low-growing or reduced yield, often observed with the constitutive expression in the entire plant. An additional advantage of root and above organ specific gene expression is that the resistance mediated gene products are only formed in the organ to be protected.

Genes, which gene products have an indirect antifungal activity, need a particularly careful expression control in order to avoid negative consequences of an undesired activation of the plant defense. One example for an indirect antifungal activity is the effect, which is derived from the coexpression of a plant resistance (R) gene in combination with an avirulence (avr) gene in a plant cell. Simultaneous expression of R and avr gene leads to an intensive activation of the plant defense and needs a strict regulation. The regulation is obtained by either placing the R gene and/or the avr gene under the control of the pathogen inducible promoter.

Pathogen inducible promoters, as, e.g. the Vst1 promoter from wine often show in above-ground organs of transgenetic plants in addition to a local, specific activation after infection with commercially relevant phytopathogenic fungus, an unspecific activation in the root region (Stahl et al., 1995). This promoter activation is induced by pythopathologically harmless microorganisms and renders promoters as Vst1 unsuitable for the expression of an R or avr gene. However, by an organ or tissue specific constitutive expression of the R or avr gene under the control of promoters C1 and C2, which are specific for above-ground organs, a pathogen activatible promoter like, e.g. the Vst1 promoter can be used for the expression of the corresponding avr or R gene. Thus, the R/avr gene concept can be realized organ specifically.

In order to obtain the use of the R/avr gene concept in above-ground organs of sugar beet, potato, *brassica* and *Arabidopsis thaliana*, the respective R gene is fused with the promoter C1 and C2, respectively. In the case of potato, as an R gene, e.g. the Cf-9 gene of tomato is used, and for *brassica* and *A. thaliana* the RPM1 gene from *A. thaliana* is used. The corresponding avr gene (avr9 from *Cladosporium fulvum* for potato and avrB from *Pseudomonas* spp. for *brassica* and *A. thaliana*) is transcriptionally or translationally combined with a pathogen sensitive promoter like Vst1, hcbt2 or with one of the chimeric pathogen sensitive promoters (PCT/EP99/08710, Chimeric promoters capable of mediated gene expression in plants upon pathogen infection and uses thereof). Both expression cassettes are integrated into a binary vector, like BIN19. By *A. tumefaciens* mediated transformation, the C1/C2 promoter-R-gene combinations and the fusion between pathogen sensitive promoter and avr gene are transformed into sugar beet, potato, *brassica* and *Arabidopsis thaliana*. Subsequent resistant testing shows that sugar beets transformed with the R/avr gene combination using the C1 and C2 promoters, comprise a very high resistance towards the leaf parasites *Cercospora beticola, Ramularia beticola* and *Erysiphe betas*. Resistance testing of transgenetic potatoes show a very high resistance towards *Phytophthora infestans*, and with *brassica* plants a very high resistance towards *Phoma lingam, Sclerotinia sclerotiorum* and *Cylindro-sporium concentricum* is observed. Transgenetic *A. thaliana* show a resistance towards *Peronospora parasitica*. It is a common feature of all transgenetic plants that they do not show any undesired necrosis or misformation in the root region, which would indicate an undesired activation of R/avr system.

Repression of Pathogen Defense in Non-Infected Tissues by Using Root Specific Promoters 2-1-48 and 2-1-36 or Promoters C1 and C2, which are Active in Above-Ground Organs An activation of pathogen defense in non-infected tissues may have negative consequences on the plant development and the yield due to related consequences as cell death and conversion of the cell metabolism. A trigger for the undesired activation can be the use of pathogen sensitive promoters with insufficient specificity in combination with pathogen defense genes. An example for this problem is the use of pathogen sensitive promoters for the expression of an avirulence gene in combination with the corresponding resistance gene.

Root specific promoters can be used in order to suppress an undesired activation of, e.g. pathogen sensitive promoters in the root.

Thereby, said promoters can be used for the conversion of the R/avr concept besides "background activity".

TABLE 1

Comparison of transcript accumulation of the root specific expressed gene 2-1-48 in different organs of the sugar beet Total cell RNA was isolated after sowings at various development time points (4, 6, 10, 12, 16, 22 weeks) from sink and source leaves, from petioles, taproots and lateral roots of sugar beets and investigated by an RNA blot analysis. As a hybridization probe, the cDNA fragment 2-1-48 was used. The transcript amount formed by promoter activity was quantified with the help of a phosphoimager, and is depicted in the table for each investigation time point. The background activity of the nylon filters was once determined for each filter and subtracted from the measurement values. The background value for the analysis of time points 4-10 weeks is 164.9 psl and is 215.7 psl at time points 12-22 weeks.

| Organ | 4 weeks | 6 weeks | 10 weeks | 12 weeks | 16 weeks | 22 weeks |
|---|---|---|---|---|---|---|
| source leaf | 86.4[1,4] | 53.6 | 34.9 | 0.7 | 86.5 | 19.1 |
| sink leaf | 56.1[2] | n.d.[3] | 22.1 | 34.0 | 30.8 | 8.2 |
| petiole | n.d.[3] | 74.7 | 49.4 | 72.0 | 36.0 | 16.5 |
| taproot | 2231.0 | 2506.0 | 2581.2 | 6082.8 | 1408.5 | 681.3 |
| lateral root | n.d.[3] | 1633.0 | 486.8 | 4932.2 | 1403.5 | 833.1 |

[1]As source leaf, the first leaf pair was chosen on 4 week old sugar beet.
[2]As sink leaf, the seed leaves were chosen on 4 week old sugar beet.
[3]n.d. = not done.
[4]Measurement values are given in psl (photo stimulated luminescence) units.

TABLE 2

Comparison of transcript accumulation of the root specific expressed gene 2-1-36 in different organs of the sugar beet Total cell RNA was isolated after sowings at various development time points (4, 6, 10, 12, 16, 22 weeks) from sink and source leaves, from petioles, taproots and lateral roots of sugar beets and investigated by an RNA blot analysis. As a hybridization probe, the cDNA fragment 2-1-36 was used. The transcript amount formed by promoter activity was quantified with the help of a phosphoimager, and is depicted in the table for each investigation time point. The background activity of the nylon filters was once determined for each filter and subtracted from the measurement values. The background value for the analysis of time points 4-10 weeks is 145 psl and is 212.67 psl at time points 12-22 weeks.

| Organ | 4 weeks | 6 weeks | 10 weeks | 12 weeks | 16 weeks | 22 weeks |
|---|---|---|---|---|---|---|
| source leaf | 3.4[1,4] | 2.0 | 7.8 | 0 | 9.5 | 5.5 |
| sink leaf | 0[2] | 4.8 | 7.3 | 3.6 | 12.4 | 11 |
| setiole | n.d.[3] | 9.8 | 4.7 | 5.3 | 15.4 | 13.7 |
| taproot | 67.2 | 102.7 | 136.2 | 803.3 | 546.4 | 518.7 |
| lateral root | n.d.[3] | 71.5 | 177.4 | 888.0 | 363.1 | 874.0 |

[1]As source leaf, the first leaf pair was chosen on 4 week old sugar beet.
[2]As sink leaf, the seed leaves were chosen on 4 week old sugar beet.
[3]n.d. = not done.
[4]Measurement values are given in psl (photo stimulated luminescence) units.

TABLE 3

Comparison of transcript accumulation of gene 2-3-9 in different organs of sugar beet Total cell RNA was isolated after sowings at various development time points (4, 6, 10, 12, 16, 22 weeks) from sink and source leaves, from petioles, taproots and lateral roots of sugar beets and investigated by an RNA blot analysis. As a hybridization probe, the cDNA fragment 2-3-9 was used. The transcript amount formed by promoter activity was quantified with the help of a phosphoimager, and is depicted in the table for each investigation time point. The background activity of the nylon filters was determined on four independent positions, respectively, and the mean value of the background was subtracted from the measurement values. The background values for the analysis of the time points 4-10 weeks are 155.1 psl as a mean value (individual values: 150.7; 150.1; 141.7 and 177.9), and at time points 12-22 weeks the mean value is 155.9 psl (individual values: 149.3; 150.4; 178.3 and 145.8).

| Organ | 4 weeks | 6 weeks | 10 weeks | 12 weeks | 16 weeks | 22 weeks |
|---|---|---|---|---|---|---|
| source leaf | 3788[1,4] | 2084.2 | 249.6 | 1117.9 | 2073.7 | 1634.4 |
| sink leaf | 1927.7[2] | 2239.3 | 2067.7 | 3976.2 | 3471.2 | 4269.6 |
| petiole | n.d.[3] | 1237.2 | 960 | 1589.7 | 1140.6 | 774.1 |
| taproot | 0 | 14.2 | 0 | 17.8 | 27.3 | 13.2 |
| lateral root | n.d.[3] | 0 | 0 | 19.4 | 26.5 | 0 |

[1]As source leaf, the first leaf pair was chosen on 4 week old sugar beet.
[2]As sink leaf, the seed leaves were chosen on 4 week old sugar beet.
[3]n.d. = not done.
[4]Measurement values are given in psl (photo stimulated luminescence) units.

TABLE 4

Detection of C1 promoter activity in sugar beet leaves by ballistic transformation

| construct | leaf type | plate 1 Photinus/Renilla luciferase activity[1] | plate 2 Photinus/Renilla luciferase activity[1] | plate 3 Photinus/Renilla luciferase activity[1] | plate 1 normal. gene expression[2] | plate 2 normal. gene expression[2] | plate 3 normal. gene expression[2] | mean value normal. gene expression[2] |
|---|---|---|---|---|---|---|---|---|
| pc1L-1097 | small | 8590 119120 | 6294 91725 | 24431 294751 | 7.8 | 7.7 | 8.6 | 8.0 |
| pc1L-1097 | large | 16149 278403 | 8078 131141 | 9253 72079 | 6.0 | 6.8 | 16.1 | 9.6 |
| pc1L-7126 | small | 4751 192866 | 4811 175901 | 6008 144327 | 2.5 | 2.8 | 4.4 | 3.2 |
| pc1L-7126 | large | 13465 246870 | 8571 87835 | 1231 42334 | 5.7 | 11.6 | 3.6 | 7.0 |

TABLE 4-continued

Detection of C1 promoter activity in sugar beet leaves by ballistic transformation

| construct | leaf type | plate 1 Photinus/ Renilla luciferase activity[1] | plate 2 Photinus/ Renilla luciferase activity[1] | plate 3 Photinus/ Renilla luciferase activity[1] | plate 1 normal. gene expression[2] | plate 2 normal. gene expression[2] | plate 3 normal. gene expression[2] | mean value normal. gene expression[2] |
|---|---|---|---|---|---|---|---|---|
| without DNA | small | 228 |  |  |  |  |  |  |
|  |  | 12500 |  |  |  |  |  |  |
| without DNA | large | 300 |  |  |  |  |  |  |
|  |  | 16369 |  |  |  |  |  |  |

[1]relative light units
[2]the normalized expression values are calculated as follows:
(Photinus measured value$_{(construct)}$ − Photinus measured value$_{(without\ DNA)}$/Renilla measured value$_{(construct)}$ − Renilla measured value$_{(without\ DNA)}$) × 100.

LITERATURE

Altschul, S. F. et al. (1990). Basic Local Alignment search tool, J. Mol. Biol. 215: 403-410

An, G. (1987). Binary Ti vectors for plant transformation and promoter analysis. Methods Enzymol. 153, 292-305.

Berghall, S., Briggs, S., Elsegood, S. E., Eronen, L., Kuusisto, J. O., Philip, E. J., Theobald, T. C., and Walliander, P. (1997). The role of sugar beet invertase related enzymes during growth, storage and processing. Zuckerind. 122, 520-530.

Cai, D. et al., (1997). Positional cloning of a gene for nematode resistance in sugar beet. Science 275, 832-834.

DE 4207358 A1 (Institut Par Genbiologische Forschung Berlin GmbH). Expressionskassette und Plasmid zur schliesszellenspezifischen Expression und ihre Verwendung zur Her-stellung transgener Pflanzenzellen und Pflanzen.

De Greve, H., Dhaese, P., Seurinck, J., Lemmers, M., Van Montagu, M., and Schell, J. (1982). Nucleotide sequence and transcript map of the Agrobacterium tumefaciens Ti plasmid-encoded Octopine synthase gene. J. Mol. Appl. Genet. 1 (6), 499-511.

Depicker, A., Stachel, S., Dhaese, P. Zambryski, P., and Goodman, H. M. (1982). Nopaline synthase: Transcript mapping and DNA sequence. J. Mol. Appl. Genet. 1 (6), 561-573.

Diatchenko, L., Lau, Y.-F. C., Campbell, A. P., Chenchik, A., Moqadam, F., Huang, B., Lukyanov, S., Lukyanov, K., Gurskaya, N., Sverdlov, E. D., and Siebert, P. D. (1996). Suppression subtractive hybridization: A method for generating differentially regulated or tissue-specific cDNA probes and libraries. Proc. Natl. Acad. Sci. USA 93, 6025-6030.

Dzelzkalns, V. A., Thorsness, M. K., Dwyer, K. G., Baxter, J. S., Balent, M. A., Nasrallah, M. E., and Nasrallah, J. B. (1993). Distinct cis-acting elements direct pistil-specific and pollen-specific activity of the Brassica S locus glycoprotein gene promoter. Plant Cell 5, 855-863.

EP 0344029 B1. (Plant Genetic Systems, N.V. 1040 Brussel). Plants with modified stamen cells.

EP 99/08710, Chimeric promoters capable of mediating gene expression in plants upon pathogen infection and uses thereof.

Giuliano, G., Pichersky, E., Malik, V. S., Timko, M. P., Scolnik, P. A., and Cashmore, A. R. (1988). An evolutionarily conserved protein binding sequence upstream of a plant light regulated gene. Proc. Natl. Acad. Sci. USA 85, 7089-7093.

Greiner, S., Krausgrill, S., and Rausch, T. (1998). Cloning of a tobacco apoplasmic invertase inhibitor: Proof of function of the recombinant protein and expression analysis during plant development. Plant Physiol. 116, 733-742.

Hesse, H., and Willmitzer, L. (1996). Expression analysis of a sucrose synthase gene from sugar beet (Beta vulgaris L.). Plant Mol Biol 30, 863-872.

Höfgen R. & Hesse H.: DE 19607697, granted 09-04-1998/ WO 97/32027, published Apr. 9, 1997

Horsch, R. B., Fry, J. E., Hoffmann, N. L., Rogers, S. G., Fraley, R. T. (1985). A simple and general method for transferring genes into plants. Science 227, 1229-1231.

Klein. K. (1995). Die Bedeutung von Saccharose-Stoffwechselgenen far die bakterielle Isomaltulose-Herstellung. Dissertation Universisität Stuttgart.

Lam, E. and Chua, N. H. (1989). ASF-2: A factor that binds to the cauliflower mosaic virus 35S promoter and a conserved GATA motif in cab promoters. Plant Cell 1, 1147-1156.

Logemann, J., Schell, J., and Willmitzer, L. (1987). Improved method for the isolation of RNA from plant tissue. Anal. Biochem. 163, 16-20.

Odell, J. T. Nagy, F., and Chua, N.-H. (1985). Identification of DNA sequences required for activity of the cauliflower mosaic virus 35S promoter. Nature 313, 810-812.

Piechulla, B., Merforth, N., and Rudolph, B. (1999). Identification of tomato Lhc promoter regions necessary for circadian expression. Plant Mol. Biol. 38, 655-662.

Saghai-Maroof, M. A., Solimanm, K. M., Jorgensen, R. A., ans Allard, R. W. (1984). Ribosomal DNA spacer length polymorphism in barley: mendelian inheritance, chromosomal location and population dynamics. Proc. Natl. Acad. Sci. USA 81, 8014-8018.

Sambrook, J., Fritsch, E. F., and Maniatis, T (1989). In Molecular Cloning, A Laboratory Manual. (Cold Spring Harbor Laboratory Press, New York).

Stahl, D. J., Fischer, R., Dettendorfer, J., Sauerbrey, E., Hain, R., and Nehls, R. (1995). Molecular analysis of the pathogen induced expression of the resveratrol synthase gene in transgenic plants. 4th International Workshop on Pathogenesis related proteins in plants: Biology and biotechnological potential. Kloster Irsee, September 3-7.

US 005608150A (Monsanto Company). Fruit specific promoters.

Van der Vossen, E. A. G., Rouppe van der Voort, J. N. A. M., Kanyuka, K., Bendahmane, A., Sandbrink, H., Baulcombe, D. C., Bakker, J., Stiekema, W. J., and Klein-Lankhorst, R. M. (2000). Homologues of a single resistance—gene cluster in potato confer resistance to distinct pathogens: a virus and a nematode. Plant Journal 23(5), 567-576., Velten, J., Velten, L., Hain, R., and Schell, J. (1984). Isolation of a dual promoter fragment from Ti plasmid of *Agrobacterium tumefaciens*. EMBO J. 12, 2723-2730.

WO 94/02619 (Pioneer Hi-Breed International, Inc.) A brassicae regulatory sequence for root-specific or root abundant gene expression.

WO 97/28268 (The Minister of Agriculture and Agri-Food Canada). Promoter from tobacco.

WO 97/27307 (Agritope, Inc). Raspberry promoters for expression of transgenes in plants.

WO 97/32027 (Max-Planck-Gesellschaft zur Förderung der Wissenschaften). Sugarbeet storage-root-tissue-specific regulon.

WO 98/18940 (BASF Aktiengesellschaft). Leaf-specific gene expression in transgenic plants.

WO/98/45460 (Rhone-Poulenc Agro). A sunflower albumin 5' regulatory region for the modification of plant seed lipid composition.

Zhou, D. X. (1999). Regulatory mechanism of plant gene transcription by GT-elements and GT-factors. Trends in Plant Sciences 4, 210-214.

The invention claimed is:

1. An isolated promoter, which is active in above-ground plant parts, comprising a nucleic acid sequence selected from the group consisting of:
   a. SEQ ID NO: 3;
   b. the polynucleotide sequence complementary to the full length of SEQ ID NO: 3;
   c. a fragment of SEQ ID NO: 3 providing promoter activity in above-ground plant parts; and
   d. a fragment of a sequence complementary to the full length of SEQ ID NO: 3, wherein said fragment provides promoter activity in above-ground plant parts.

2. The isolated promoter of claim 1 inserted into a vector or operably connected to a mobile genetic element.

3. A transgenic eukaryotic or a transgenic prokaryotic host cell comprising a promoter, which is active in above-ground plant parts, that is operably linked to a transgene, wherein said promoter comprises a nucleotide sequence selected from the group consisting of:
   a. SEQ ID NO: 3 having a promoter activity;
   b. the polynucleotide sequence complementary to the full length of SEQ ID NO: 3;
   c. a fragment of SEQ ID NO: 3 providing promoter activity in above-ground plant parts; and
   d. a fragment of a sequence complementary to the full length of SEQ ID NO: 3, wherein said fragment provides promoter activity in above-ground plant parts.

4. A transgenic plant comprising a promoter that is active in above-ground plant parts and that is operably linked to a transgene, wherein said promoter comprises a nucleotide sequence selected from the group consisting of:
   a. SEQ ID NO: 3 having a promoter activity;
   b. a sequence complementary to the full length of SEQ ID NO: 3;
   c. a fragment of SEQ ID NO: 3 providing promoter activity in above-ground plant parts; and
   d. a fragment of a sequence complementary to the full length of SEQ ID NO: 3, wherein said fragment provides promoter activity in above-ground plant parts.

5. The transgenic plant according to claim 4, wherein said transgenic plant is *Beta vulgaris*, and wherein said promoter is active in the above-ground plant parts of *Beta vulgaris*.

6. The transgenic plant according to claim 4, wherein said transgenic plant is further characterized by the expression of a transgene exclusively in an above-ground plant part, wherein said expression is obtainable by transformation of a plant cell with said promoter that is operably linked to a transgene.

7. A transgenic seed produced by said transgenic plant of claim 4.

8. The transgenic plant according to claim 6, wherein said above-ground plant part is a leaf.

9. The transgenic plant according to claim 6, wherein said plant belongs to species *Beta vulgaris*, and wherein said promoter is active in the above-ground plant parts of *Beta vulgaris*.

10. The transgenic plant according to claim 6, wherein said transgenic plant is characterized by:
    a. amending a carbohydrate metabolism;
    b. avoiding a loss of a storage substance;
    c. expressing an invertase inhibitor;
    d. expressing a fructosyl transferase;
    e. expressing a levan sucrose;

f. expressing a gene coding for a transporter protein for a N-compound; or
g. developing a feature that increases at least one of resistance and tolerance towards pathogens.

11. A method of:
a. amending carbohydrate metabolism,
b. avoiding loss of storage substance,
c. increasing at least one of resistance and tolerance towards a pathogen, or
d. expressing from a transgene:
an invertase inhibitor,
a fructosyl transferase,
a levan sucrose, or
a transporter protein for a N-compound, in a transgenic plant, said method comprising:
(1) transforming a plant cell with a promoter, which is active in above-ground plant parts, wherein said promoter is operably linked to said transgene, and
(2) subsequently regenerating a transgenic plant from said plant cell,
wherein said promoter comprises a nucleotide sequence selected from the group consisting of:
i. SEQ ID NO: 3;
ii. the polynucleotide sequence complementary to the full length of SEQ ID NO: 3;
iii. a fragment of SEQ ID NO: 3 providing promoter activity in above-ground plant parts; and
iv. a fragment of a sequence complementary to the full length of SEQ ID NO: 3, wherein said fragment provides promoter activity in above-ground plant parts 12. An isolated promoter comprising a nucleotide sequence selected from the group consisting of:
a. SEQ ID NO: 3; and
b. the polynucleotide sequence complementary to the full length of SEQ ID NO: 3.

13. The isolated promoter of claim 12 inserted into a vector or operably connected to a mobile genetic element.

14. A transgenic eukaryotic or a transgenic prokaryotic host cell comprising a promoter that is operably linked to a transgene, wherein said promoter comprises a nucleotide sequence selected from the group consisting of:
a. SEQ ID NO: 3 having a promoter activity; and
b. the polynucleotide sequence complementary to the full length of SEQ ID NO: 3.

15. A transgenic plant comprising a promoter that is operably linked to a transgene, wherein said promoter comprises a nucleotide sequence selected from the group consisting of:
a. SEQ ID NO: 3 having a promoter activity; and
b. the polynucleotide sequence complementary to the full length of SEQ ID NO:3.

16. The transgenic plant according to claim 15 wherein said transgenic plant is *Beta vulgaris*, and wherein said promoter is active in the above-ground plant parts of *Beta vulgaris*.

17. The transgenic plant according to claim 15, wherein said transgenic plant is further characterized by the expression of a transgene exclusively in an above-ground plant part, wherein said expression is obtainable by transformation of a plant cell with said promoter that is operably linked to a transgene.

18. A transgenic seed produced by said transgenic plant of claim 15.

19. The transgenic plant according to claim 17, wherein said above-ground plant part is a leaf.

20. The transgenic plant according to claim 17, wherein said plant belongs to species *Beta vulgaris*, and wherein said promoter is active in the above-ground plant parts of *Beta vulgaris*.

21. The transgenic plant according to claim 17, wherein said transgenic plant is characterized by:
a. amending a carbohydrate metabolism;
b. avoiding a loss of a storage substance;
c. expressing an invertase inhibitor;
d. expressing a fructosyl transferase;
e. expressing a levan sucrose;
f. expressing a gene coding for a transporter protein for an N-compound; or
g. developing a feature that increases at least one of resistance and tolerance towards pathogens.

22. A method of:
a. amending carbohydrate metabolism;
b. avoiding loss of storage substance;
c. increasing at least one of resistance and tolerance towards a pathogen; or
d. expressing from a transgene:
an invertase inhibitor,
a fructosyl transferase,
a levan sucrose, or
a transporter protein from an N-compound, in a transgenic plant, said method comprising:
(1) transforming a plant cell with a promoter, wherein said promoter is operably linked to said transgene; and
(2) subsequently regenerating a transgenic plant from said plant cell, wherein said promoter comprises a nucleotide sequence selected from the group consisting of:
i. SEQ ID NO: 3; and
ii. the polynucleotide sequence complementary to SEQ ID NO: 3.

* * * * *